(12) United States Patent
Threadgill et al.

(10) Patent No.: US 8,703,769 B2
(45) Date of Patent: Apr. 22, 2014

(54) USE OF EGFR INHIBITORS TO PREVENT OR TREAT OBESITY

(75) Inventors: David Threadgill, Chapel Hill, NC (US); Cordelia Johnson Barrick, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 389 days.

(21) Appl. No.: 11/887,014

(22) PCT Filed: Jul. 14, 2006

(86) PCT No.: PCT/US2006/027316
§ 371 (c)(1),
(2), (4) Date: Jan. 23, 2009

(87) PCT Pub. No.: WO2007/011702
PCT Pub. Date: Jan. 25, 2007

(65) Prior Publication Data
US 2009/0202529 A1    Aug. 13, 2009

Related U.S. Application Data

(60) Provisional application No. 60/699,671, filed on Jul. 15, 2005.

(51) Int. Cl.
*A61K 31/495* (2006.01)
*A01N 43/54* (2006.01)

(52) U.S. Cl.
USPC ......... 514/248; 514/258.1; 514/267; 514/910

(58) Field of Classification Search
USPC ............................... 514/248, 258.1, 267, 910
See application file for complete search history.

(56) References Cited

U.S. PATENT DOCUMENTS

| | | | |
|---|---|---|---|
| 4,196,265 A | 4/1980 | Koprowski et al. | |
| 5,234,933 A | 8/1993 | Marnett et al. | |
| 5,326,902 A | 7/1994 | Seipp et al. | |
| 5,352,660 A | 10/1994 | Pawson | |
| 5,422,245 A | 6/1995 | Nielsen et al. | |
| 5,627,158 A | 5/1997 | Cho-Chung | |
| 5,645,999 A | 7/1997 | Roberts et al. | |
| 5,723,115 A | 3/1998 | Serrero | |
| 5,734,033 A | 3/1998 | Reed | |
| 5,739,278 A | 4/1998 | Daum et al. | |
| 5,786,152 A | 7/1998 | Marengere et al. | |
| 5,837,479 A | 11/1998 | Young et al. | |
| 6,656,907 B1 * | 12/2003 | Buret et al. | 514/12 |
| 7,232,897 B2 * | 6/2007 | Hotamisligil et al. | 536/7.4 |

FOREIGN PATENT DOCUMENTS

| | | |
|---|---|---|
| CA | 2359180 | 8/2000 |
| WO | WO93/25521 | 12/1993 |
| WO | WO99/07409 | 2/1999 |
| WO | WO99/32619 | 7/1999 |
| WO | WO00/01846 | 1/2000 |
| WO | WO00/44895 | 8/2000 |
| WO | WO00/44914 | 8/2000 |
| WO | WO00/63364 | 10/2000 |
| WO | WO01/04313 | 1/2001 |
| WO | WO01/29058 | 4/2001 |
| WO | WO01/36646 | 5/2001 |
| WO | WO01/68836 | 9/2001 |
| WO | WO01/75164 | 10/2001 |
| WO | WO01/92513 | 12/2001 |
| WO | WO02/44321 | 6/2002 |
| WO | WO02/055692 | 7/2002 |
| WO | WO02/055693 | 7/2002 |
| WO | WO03/006477 | 1/2003 |
| WO | WO2007/011702 | 1/2007 |

OTHER PUBLICATIONS

Bianco R. et al. "Rational basis for the development of EGFR inhibitors for cancer treatment". The International Journal of Biochemistry & Cell Biology 39 (2007) 1416-1431.*
Abou-Rjaily et al., "CEACAM1 Modulates Epidermal Growth Factor Receptor-Mediated Cell Proliferation," The Journal of Clinical Investigation, vol. 114, No. 7, pp. 944-952 (Oct. 2004).
Laskin et al., "Epidermal growth factor receptor: A Promising Target in Solid Tumours," Cancer Treatment Reviews, vol. 30, pp. 1-17 (2004).
Menendez et al., "Orlistat: From Antiobesity Drug to Anticancer Agent in Her-2/neu (erbB-2)-Overexpressing Gastrointestinal Tumors?" Exp. Biol. Med., vol. 230, pp. 151-154 (Mar. 2005).
Menendez et al., "The Antiobesity Drug Orlistat Induces Cytotoxic Effects, Suppresses Her-2/neu (erbB-2) Ongogene Overexpression, and Synergistically Interacts with Trastuzumab (Herceptin™) in Chemoresistant Ovarian Cancer Cells," Int. J. Gynecol. Cancer, vol. 16, pp. 219-221 (2006).
Notification of Transmittal of the International Search Report and the Written Opinion of the International Searching Authority, or the Declaration for International Application No. PCT/US06/027316 (Feb. 6, 2008).

(Continued)

*Primary Examiner* — Renee Claytor
(74) *Attorney, Agent, or Firm* — Jenkins, Wilson, Taylor & Hunt, P.A.

(57) ABSTRACT

Methods of treating or preventing obesity or obesity related disorders in a subject are provided, comprising administering to the subject a treatment effective in reducing one or more activities of an epidermal growth factor receptor (EGFR) in the subject. Methods of screening for compositions that can modulate one or more EGFR activities are also provided.

23 Claims, 24 Drawing Sheets

(56) References Cited

OTHER PUBLICATIONS

Pagano et al., "ErbB2 and EGFR Are Downmodulated During the Differentiation of 3T3-L1 Preadipocytes," Journal of Cellular Biochemistry, vol. 90, pp. 561-572 (2003).
Bass, "The short answer," Nature. vol. 411 pp. 428-429 (2001).
Batzer et al., "Enhanced evolutionary PCR using oligonucleotides with inosine at the 3'-terminus," Nucleic Acids Research. vol. 19, No. 18 p. 5081 (1991).
Bernstein et al., "Role for a bidentrate ribonuclease in the initiation step of RNA interference," Nature. vol. 409 pp. 363-366 (2001).
Bray et al., "Sibutramine Produces Dose-Related Weight Loss," Obesity Research. vol. 7, No. 2 pp. 189-198 (1999).
Brommage, "Validation and calibration of Dexa body composition in mice," Am. J. Physiol. Endocrinol. Metab. vol. 285 pp. E454-E459 (2003).
Cuadrado et al., "JNK activation is critical for Aplidin™-induced apoptosis," Oncogene. vol. 23 pp. 4673-4680 (2004).
Davidson et al., "Weight Control and Risk Factor Reduction in Obese Subjects Treated for 2 Years With Orlistat," JAMA. vol. 281, No. 3 pp. 235-242 (1999).
Douglas et al., "Plasma Phentermine Levels, Weight Loss and Side-Effects," International Journal of Obesity. vol. 7, No. 6 pp. 591-595 (1983).
Eguchi et al., "Activation of MAPKs by Angiotensin II in Vascular Smooth Muscle Cells," The Journal of Biological Chemistry. vol. 276, No. 11 pp. 7957-7962 (2001).
El Marjou et al., "Tissue-Specific and Inducible Cre-Mediated Recombination in the Gut Epithelium," Genesis. vol. 39 pp. 186-193 (2004).
Elbashir et al., "Duplexes of 21-nucleotide RNAs mediate RNA interference in cultured mammalian cells," Nature. vol. 411 pp. 494-498 (2001).
Elbashir et al., "RNA interference is mediated by 21- and 22-nucleotide RNAs," Genes & Development. vol. 15 pp. 188-200 (2001).
Fire, "RNA-triggered gene silencing," TIG. vol. 15, No. 9 pp. 358-363 (1999).
Fire et al., "Potent and specific genetic interference by double-stranded RNA in *Caenorhabditis elegans*," Nature. vol. 391 pp. 806-811 (1998).
Goldstein et al., "Biological Efficacy of a Chimeric Antibody to the Epidermal Growth Factor Receptor in a Human Tumor Xenograft Model," Clinical Cancer Research. vol. 1 pp. 1311-1318 (1995).
Grundy, S.M., and Barnett, J.P., "Metabolic and Health Complications of Obesity," Dis. Mon. vol. 36, No. 12 pp. 645-696 (1990).
Guy-Grand et al., "International Trial of Long-Term Dexfenfluramine in Obesity," The Lancet. vol. pp. 1142-1145 (1989).
Hammond et al., "An RNA-directed nuclease mediates post-transcriptional gene silencing in *Drosophila cells*," Nature. vol. 404 pp. 293-296 (2000).
Herbst et al., "Gefitinib—a novel targeted approach to treating cancer," Nature Reviews. vol. 4 pp. 956-965 (2004).
Luetteke et al., "The mouse *waved*-2 phenotype results from a point mutation in the EGF receptor tyrosine kinase," Genes & Development. vol. 8 pp. 399-413 (1994).
Nishina et al., "Atherosclerosis in Genetically Obese Mice: The Mutants Obese, Diabetes, Fat, Tubby, and Lethal Yellow," Metabolism. vol. 43, No. 5 pp. 554-558 (1994).
Notification Concerning Transmittal of International Preliminary Report on Patentability (Chapter I of the Patent Cooperation Treaty) corresponding to International Patent Application No. PCT/US2006/027316 dated Mar. 19, 2009.
Nykanen et al., "ATP Requirements and Small Interfering RNA Structure in the RNA Interference Pathway," Cell. vol. 107 pp. 309-321 (2001).
Ohtsuka et al., "An Alternative Approach to Deoxyoligonucleotides as Hybridization Probes by Insertion of Deoxyinosine at Ambiguous Codon Positions," The Journal of Biological Chemistry. vol. 260, No. 5 pp. 2605-2608 (1985).
Rossolini et al., "Use of deoxyinosine-containing primers vs degenerate primers for polymerase chain reaction based on ambiguous sequence information," Molecular and Cellular Probes. vol. 8 pp. 91-98 (1994).
Takeuchi et al., "Mitogen-activated protein kinase phophatase-1 modulated JNK activation is critical for apoptosis induced by inhibitor of epidermal growth factor receptor-tyrosine kinase," FEBS Journal. vol. 276 pp. 1255-1265 (2009).
Threadgill et al., "Targeted Disruption of Mouse EGF Receptor: Effect of Genetic Background on Mutant Phenotype," Science. vol. 269, No. 5221 pp. 230-234 (1995).
Wianny, F. and Zernicka-Goetz, M., "Specific interference with gene function by double-stranded RNA in early mouse development," Nature Cell Biology. vol. 2 pp. 70-75 (2000).
Yarden, "The EGFR family and its ligands in human cancer: signalling mechanisms and therapeutic opportunities," European Journal of Cancer. vol. 37 pp. S3-S8 (2001).
Zhuo et al., "hGFAP-cre Transgenic Mice for Manipulation of Glial and Neuronal Function in Vivo," Genesis. vol. 31 pp. 85-94 (2001).
Barrick et al., "Chronic pharmacologic inhibition of EGFR leads to cardiac dysfunction in C57BL/6J mice," Toxicology and Applied Pharmacology. vol. 228 pp. 315-325 (2008).
Forsyth et al., "Regulation of Oxidant-Induced Intestinal Permeability by Metalloprotease-Dependent Epidermal Growth Factor Receptor Signaling," The Journal of Pharmacology and Experimental Therapeutics. vol. 321, No. 1 pp. 84-97 (2007).
Garcia-Martinez et al., "Intestinal Gluocse Absorption Is Lower in Obese than in Lean Zucker Rats," J. Nutrition. vol. 123 pp. 1062-1067 (1993).
Melichar et al., "Intestinal permeability, vitamin A absorption and serum alpha-tocopherol during therapy with gefitinib," Scand. J. Clin. Lab. Invest. vol. 70, No. 3 pp. 180-187 (2010) [Abstract].
Scheving et al., "Epidermal Growth Factor Receptor of the Intestinal Enterocyte," The Journal of Biological Chemistry. vol. 264, No. 3 pp. 1735-1741 (1989).
Sigalet et al., "A pilot study of the use of epidermal growth factor in pediatric short bowel syndrome," Journal of Pediatric Surgery. vol. 40 pp. 763-768 (2005).

\* cited by examiner

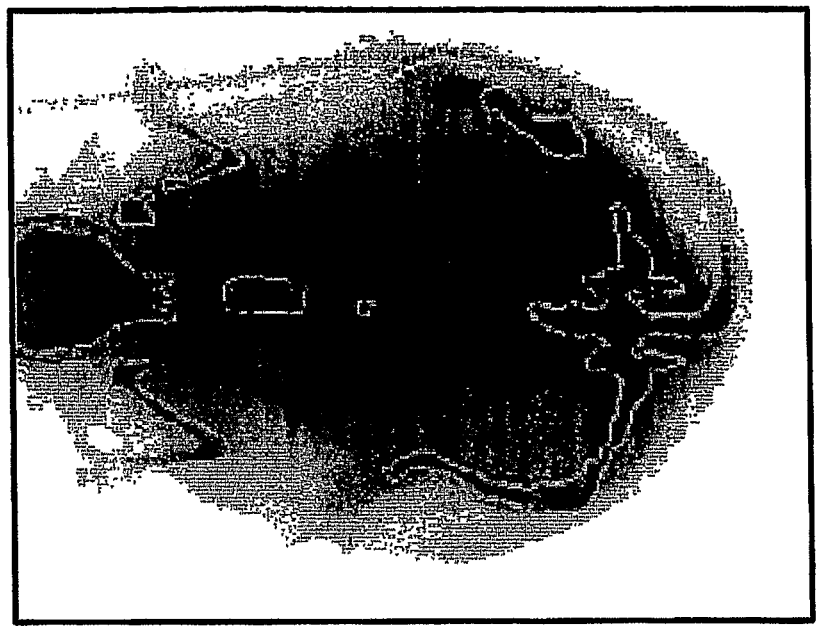
A
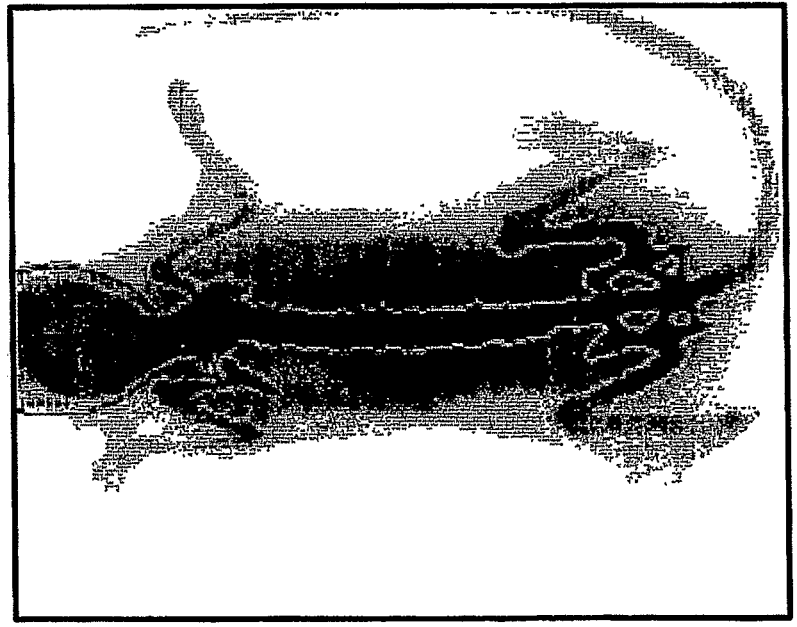
B
FIG. 2

USE OF EGFR INHIBITORS TO PREVENT OR TREAT OBESITY

CROSS-REFERENCE TO RELATED APPLICATIONS

This application claims the benefit of U.S. Provisional Patent Application Ser. No. 60/699,671, filed Jul. 15, 2005; the disclosure of which is incorporated herein by reference in its entirety.

GOVERNMENT INTEREST

The presently disclosed subject matter was made with U.S. government support under Grant No. R01-CA092479 awarded by the U.S. National Institutes of Health (NIH). As such, the U.S. government has certain rights in the present subject matter.

TECHNICAL FIELD

The presently disclosed subject matter relates to compositions and methods for treating or preventing obesity and/or obesity-related disorders. In particular, the presently disclosed subject matter relates to compositions and methods for treating or preventing obesity by reducing one or more biological activities of an epidermal growth factor receptor (EGFR).

ABBREVIATIONS ab=antibody
BF=body fat
BMI=body mass index
BSA=bovine serum albumin
BW=body weight
° C.=degrees Celsius
DEXA=dual-energy x-ray absorptiometry
dsRNA=double stranded RNA
EGF=epidermal growth factor
EGFR=epidermal growth factor receptor
F=female
g=grams
GFAP=human glial fibrillary acidic protein promoter
h=hours
HFD=high fat diet
kg=kilograms
KLH=keyhole limpet hemocyanin
M=male
mL=milliliters
mm=millimeters
mM=millimolar
mosm/L=milliosmols per liter
NCBI=National Center for Biotechnology Information
ORF=open reading frame
PKR=RNA-dependent protein kinase
RISC=RNA-induced silencing complex
RNAi=RNA interference
siRNA=small interfering RNA
TGF=transforming growth factor
wa2=waved-2 allele
wt=wild-type

BACKGROUND

During times of nutritional excess, mammals store excess energy in adipocytes (fat cells). During times of nutritional insufficiency, triglycerides stored in the adipocytes are degraded to fatty acids and released to provide required energy. Many humans, for example, are not subjected to extended periods of low caloric intake, and as such, experience the accumulation of adipose tissue, leading to obesity.

There are several health risks associated with obesity, including the development of insulin resistance, hypertension, atherosclerosis, dyslipidemia, coronary heart disease, stroke, gallbladder disease, osteoarthritis, liver cirrhosis, sleep apnea and respiratory problems, and some cancers (endometrial, breast, and colon). Since most of these disorders are chronic conditions, they are expected to lead to rising medical costs and to create serious problems for society. Furthermore, despite the fact that these consequences of obesity have become well known in developed countries, the prevalence of obesity is rising rather than falling.

Obesity and obesity-related disorders are often treated by encouraging patients to lose weight by reducing their food intake or by increasing their exercise level, thereby increasing their energy output. A sustained weight loss of 5% to 10% of body weight has been shown to improve the co-morbidities associated with obesity and can lead to improvement of obesity-related disorders.

Weight loss drugs used for the treatment of obesity include orlistat (Davidson, M. H. et al. (1999) JAMA 281:23542), dexfenfluramine (Guy Grand, B. et al. (1989) Lancet 2:1142-5), sibutramine (Bray, G. A. et al. (1999) Obes. Res. &:189-98) and phentermine (Douglas, A. et al. (1983) Int. J. Obes. 7:591-5). However, the side effects of these drugs and anti-obesity agents can limit their use. Dexfenfluramine was withdrawn from the market because of suspected heart valvulopathy; orlistat is limited by gastrointestinal side effects; and the use of sibutramine is limited by its cardiovascular side effects, which have led to reports of deaths and its withdrawal from the market in at least Italy.

Some of the presently known target molecules in anti-obesity research include leptin, PPAR-γ and neuropeptide Y. But, because of the huge variety of causes for obesity, it is desirable to focus on molecules having different action mechanisms as targets for future drug development.

What are needed, then, are new methods and compositions for treating and/or preventing obesity. This and other needs in the art are addressed in whole or in part by the presently disclosed subject matter.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In one embodiment of the presently disclosed subject matter, a method of treating or preventing obesity in a subject is provided. In some embodiments, the method comprises administering to the subject a treatment effective in reducing an activity of an epidermal growth factor receptor (EGFR) in the subject, whereby obesity in the subject is treated or prevented.

In another embodiment of the presently disclosed subject matter, a method of treating or preventing a disorder associated with obesity in a subject in need of such treatment is provided. In some embodiments, the method comprises administering to the subject a treatment effective in reducing an activity of an EGFR in the subject. In some particular embodiments, the disorder associated with obesity is selected from the group consisting of heart disease, hypertension, stroke, Type II diabetes, arthritis, insulin resistance, atherosclerosis, coronary artery disease, hyperlipidemia, gallbladder disease, osteoarthritis, sleep apnea, liver cirrhosis, and cancer.

In some embodiments of the therapeutic methods, the step of administering comprises administering an effective amount of a composition that modulates expression of the EGFR in the subject. In some of these embodiments, the composition that modulates expression of the EGFR comprises an antisense oligonucleotide. In other embodiments of the therapeutic methods, the step of administering comprises administering an effective amount of a composition comprising an EGFR binding molecule that reduces the activity of the EGFR. In some embodiments, the EGFR binding molecule comprises an EGFR kinase inhibitor, including for example gefitinib, erlotinib, 4-(3-chloroanilino)-6,7-dimethoxyquinazoline, EKB-569, EKI-785, canertinib dihydrochloride, D-69491, lapatinib ditosylate, ZD6474, PKC-412, sunitinib malate, vatalanib, SU5614, CEP-701, PKC-412, MLN518, XL999, VX-322, and pharmaceutically acceptable salts thereof. In some embodiments, the EGFR binding molecule comprises an anti-EGFR antibody, including for example cetuximab, ABX-EGF, trastuzumab, and EMD 72000.

In some embodiments of the therapeutic methods, the subject is a mammal, such as for example a rodent, a swine, a ruminant, and a primate. In some embodiments, the primate is human.

In still other embodiments of the presently disclosed subject matter, a method of screening candidate substances for an ability to modulate an activity of an EGFR associated with obesity is provided. In some embodiments, the method comprises establishing replicate test and control samples that comprise a biologically active EGFR polypeptide; administering a candidate substance to the test sample but not the control sample; measuring an EGFR biological activity associated with obesity in the test and the control samples; and determining that the candidate substance modulates the EGFR biological activity if the EGFR biological activity measured for the test sample is greater or less than the EGFR biological activity measured for the control sample.

In some embodiments of the screening methods, the replicate test and control samples further comprise a cell that expresses a biologically active vertebrate EGFR polypeptide. In some embodiments, modulating the EGFR activity associated with obesity comprises inhibiting the EGFR activity. In some embodiments, the inhibited EGFR activity associated with obesity is an EGFR kinase activity.

In some embodiments, the replicate test and control samples are replicate test and control animals. In some of these embodiments, the EGFR biological activity is measured by measuring a change in the amount of adipose tissue in the test and control animals over time.

Accordingly, it is an object of the presently disclosed subject matter to provide methods and compositions for treating or preventing obesity and/or disorders associated with obesity in subjects in need of such treatment. This object is achieved in whole or in part by the presently disclosed subject matter.

An object of the presently disclosed subject matter having been stated above, other objects and advantages will become apparent to those of ordinary skill in the art after a study of the following description of the presently disclosed subject matter and non-limiting Examples.

BRIEF DESCRIPTION OF THE DRAWINGS

FIGS. 2A and 2B depict body scans of a representative C57BL/6 wild-type mouse (FIG. 2A) and a representative $Egfr^{wa2/wa2}$ C57BL/6 mouse (FIG. 2B) after about four (4) weeks on the high fat diet.

DETAILED DESCRIPTION

Figure 1:
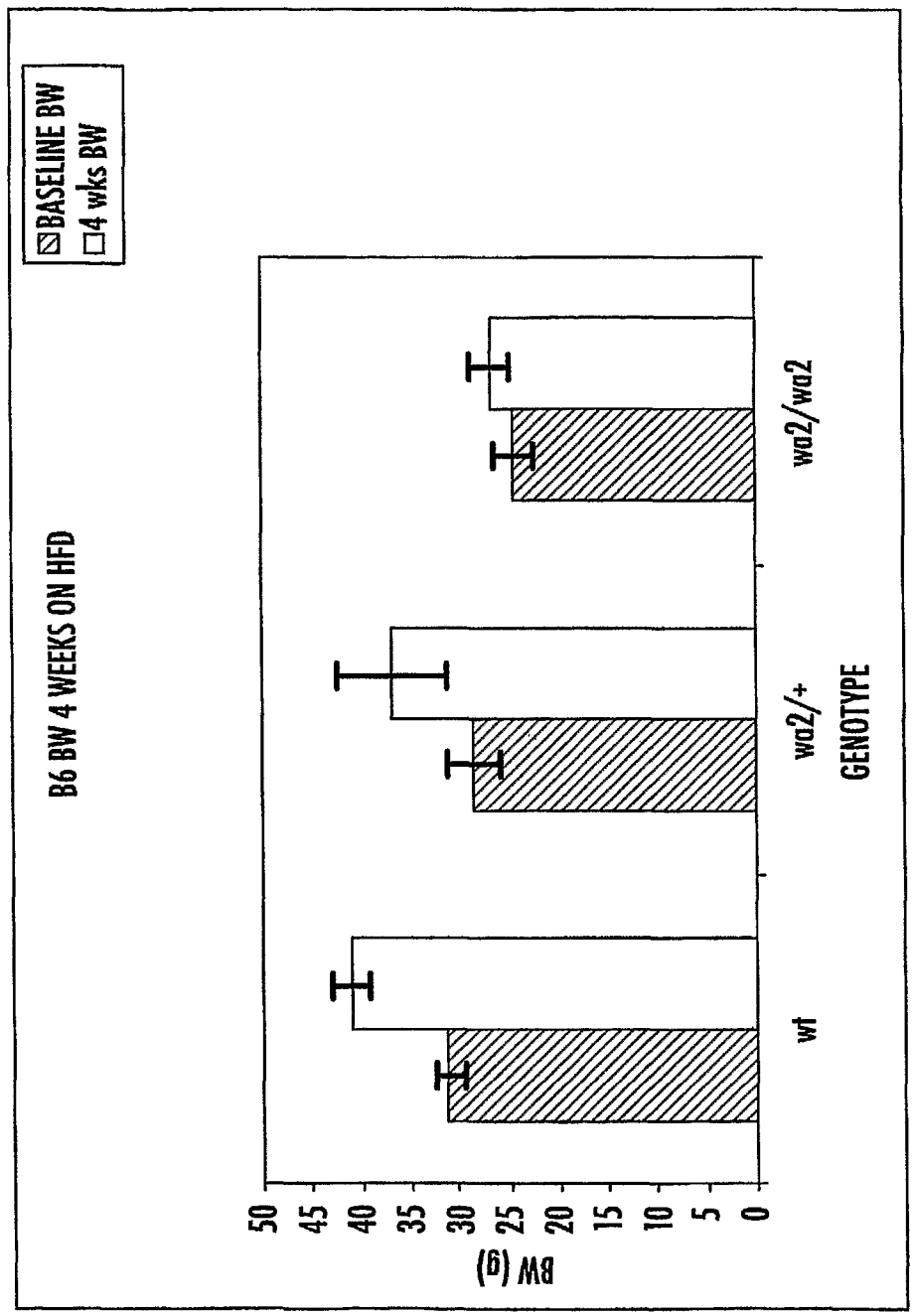
FIG. 1 is a bar graph depicting weight gains experienced by wild-type (wt) C57BL/6 mice and mice from a C57BL/6 background that were either heterozygous (wa2/+) or homozygous (wa2/wa2) for the wa2 allele of Egfr. Gray diagonal-hatched bars correspond to mouse baseline body weight (BW) and solid dark gray bars correspond to mouse body weight after four weeks.

The details of one or more embodiments of the presently disclosed subject matter are set forth in the accompanying description below. Other features, objects, and advantages of the presently disclosed subject matter will be apparent from the detailed description, drawings, and claims. All publications, patent applications, patents, and other references mentioned herein are incorporated by reference in their entirety. Some, of the polynucleotide and polypeptide sequences disclosed herein are cross-referenced to GENBANK® accession numbers. The sequences cross-referenced in the GENBANK® database are expressly incorporated by reference as are equivalent and related sequences present in GenBank® or other public databases. Also expressly incorporated herein by reference are all annotations present in the GENBANK® database associated with the sequences disclosed herein. In case of conflict, the present specification, including definitions, will control.

All technical and scientific terms used herein, unless otherwise defined below, are intended to have the same meaning as commonly understood by one of ordinary skill in the art, and references to techniques employed herein are intended to refer to the techniques as commonly understood in the art, including variations on those techniques or substitutions of equivalent techniques which would be apparent to one of skill in the art. While the following terms are believed to be well understood by one of ordinary skill in the art, the following definitions are set forth to facilitate explanation of the presently disclosed subject matter.

The presently disclosed subject matter relates to a novel target for treating or preventing obesity: the epidermal growth factor receptor (EGFR). This target already has drugs developed against it, and many of these have been shown to be well tolerated in the clinic during testing of non-obesity-related uses.

Accordingly, reduction in the biological activities of EGFR can retard accumulation of adipose tissue and/or maintain present levels of adipose tissue in a subject and mitigate the various medical risks associated with obesity.

The presently disclosed subject matter provides methods and compositions for reducing one or more biological activities of an EGFR polypeptide, including for example EGFR kinase, ligand-binding, signal transduction, and scaffolding activities. In some embodiments, the presently disclosed subject matter provides methods of reducing one or more EGFR activities by modulating expression of the EGFR. In some embodiments, the presently disclosed subject matter provides methods of reducing one or more EGFR activities by administering an effective amount of an EGFR binding molecule that can inhibit one or more EGFR activities. The presently disclosed subject matter further provides in some embodiments, methods of screening for candidate substances having an ability to modulate one or more EGFR activities.

As used herein, the terms "Egfr family member" and "Erbb family member" are used interchangeably and refer to a nucleic acid (e.g., a gene) encoding a member of the Egfr family including, but not limited to ERBB1/HER1/EGFR, ERBB2/HER2/NEU, ERBB3/HER3, and ERBB4/HER4, or a polypeptide encoded by such a nucleic acid. The EGFR family is a group of four structurally similar growth factor receptors with tyrosine-kinase activity (EGFR, HER2/neu, ErbB-3, ErbB-4), which dimerize upon binding with a number of ligands, including EGF (Epidermal Growth Factor) and TGF (Transforming Growth Factor), allowing downstream transduction of mitogenic signals. These genes and gene products are found in a diversity of species. In some embodiments, the Egfr family members are mammalian Egfr family members. Representative mammals include human, mice, and rats. With regard to particular members of the Egfr family and as indicated above, each member of the family is known by at least two different names. For example, ERBB1, HER1, and EGFR all refer to the same gene and/or gene product, as do ERBB2, HER2, and NEU.

The nucleic acid and amino acid sequences for numerous Egfr family members are present in publicly available databases (e.g. the GENBANK® database, available from the website of the National Center for Biotechnology Information (NCBI)). Nucleic acid and amino acid sequences from representative mammalian species are presented in Table 1, each of which is incorporated by reference.

TABLE 1

|  | Human | | Mouse | |
| --- | --- | --- | --- | --- |
|  | Nucleic Acid | Amino Acid | Nucleic Acid | Amino Acid |
| ERBB2 | NM_004448 | NP_004439.2 | NM_001003817 | NP_001003817 |
| ERBB3 | NM_001982 | NP_001973.2 | AY686636.1 | AAT95433.1 |
| ERBB4 | NM_005235 | NP_005226.1 | XM_136682 | XP_136682.4 |

I. Definitions

Following long-standing patent law convention, the terms "a", "an", and "the" mean "one or more" when used in this application, including the claims. For example, the phrase "a subject" refers to one subject or more than one subject.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

"Antibodies" refers to whole antibodies and antibody fragments or molecules including antibody fragments, including, but not limited to single chain antibodies, humanized antibodies, and Fab, $F(ab')_2$, $V_h$, $V_l$, Fd, and single or double chain Fv fragments.

By "construct" is meant a recombinant nucleic acid, generally recombinant DNA, which has been generated for the purpose of the expression of a specific nucleotide sequence(s), or is to be used in the construction of other recombinant nucleotide sequences.

As used herein, the term "EGFR" refers to an epidermal growth factor receptor gene or gene product. There are numerous members of the EGFR family of receptors, which have been reviewed in Yarden, 2001. The term "EGFR", as used herein, refers to EGFR specifically, as well as Egfr and Erbb family members.

Additionally, consistent with usage in the art, identifications of genes or gene products that are presented in all capital letters refer to human genes and/or gene products or are referring to a family member without reference to the species from which it is derived. For genes and gene products from non-human sources (e.g., mice), the first letter can be capitalized and other letters are presented in lower case. Also typically, references to genes are presented in italics, and references to polypeptides are presented in normal type. Thus, as used herein, EGFR refers to either a human EGFR gene or to an EGFR gene generally (i.e., without reference to a particular species). Similarly, as used herein, EGFR refers to a human EGFR polypeptide, or to an EGFR polypeptide without reference to a particular species of origin. Egfr refers to a non-human (e.g., mouse) Egfr gene, and Egfr refers to a non-human (e.g., mouse) Egfr polypeptide. Furthermore, different alleles of the ERBB family can be represented in superscript form (e.g. $Egfr^{wa2}$) or, in the absence of specific reference to the ERBB family member when the specific ERBB family member is clear, in normal-sized type (e.g., wa2). The absence of a specific superscripted allele name indicates that the allele is a wild-type allele or that the gene is being referred to generally without reference to a specific allele. The same italicization rules apply when a specific allele is identified.

The term "nucleic acid" and "nucleotide" are used interchangeably and refer to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al. (1991) *Nucleic Acid Res* 19:5081; Ohtsuka et al. (1985) *J Biol Chem* 260: 2605-2608; Rossolini et al., (1994) *Mol Cell Probes* 8:91-98). The terms "nucleic acid" or "nucleic acid sequence" can also be used interchangeably with gene, open reading frame (ORF), cDNA, and mRNA encoded by a gene.

The term "complementary" refers to two nucleotide sequences that comprise antiparallel nucleotide sequences capable of pairing with one another upon formation of hydrogen bonds between the complementary base residues in the antiparallel nucleotide sequences. As is known in the art, the nucleic acid sequences of two complementary strands are the reverse complement of each other when each is viewed in the 5' to 3' direction.

As is also known in the art, two sequences that hybridize to each other under a given set of conditions do not necessarily have to be 100% fully complementary. The terms "fully complementary" and "100% complementary" refer to sequences for which the complementary regions are 100% in Watson-Crick base-pairing, i.e., that no mismatches occur within the complementary regions. However, as is often the case with recombinant molecules (for example, cDNAs) that are cloned into cloning vectors (e.g., plasmids, cosmids, phages, viruses, and the like), certain of these molecules can have non-complementary overhangs on either the 5' or 3' ends that result from the cloning event. In such a situation, it is understood that the region of 100% or full complementarity excludes any sequences that are added to the recombinant molecule (typically at the ends) solely as a result of, or to facilitate, the cloning event. Such sequences are, for example, polylinker sequences, linkers with restriction enzyme recognition sites, etc.

The term "gene" refers broadly to any segment of DNA associated with a biological function. A gene encompasses one or more sequences including, but not limited to a coding sequence, a promoter region, a transcriptional regulatory sequence, a non-expressed DNA segment that is a specific recognition sequence for regulatory proteins, a non-expressed DNA segment that contributes to gene expression, a DNA segment designed to have desired parameters, or combinations thereof. Thus, in some embodiments the term "gene" refers to a transcription unit, including regulatory sequences that influence the transcription of the sequences present therein (e.g., enhancers).

In some embodiments, the term "gene" also refers to a natural or synthetic nucleotide-based product of a transcription unit. As such, the term refers to a primary transcription product, a partially or completely spliced transcription product (including any alternatively spliced variants), an mRNA, and a cDNA produced from an mRNA. Additionally, in some embodiments the term "gene" refers only to the protein-coding sequence of a transcription product, also referred to herein as an open reading frame (ORF).

A gene can be obtained by a variety of methods, including isolation or cloning from a biological sample, synthesis based on known or predicted sequence information, and recombinant derivation of an existing sequence.

The terms "polypeptide", "protein", and "peptide", which are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide" and "peptide" are used interchangeably herein when referring to a gene product. Thus, exemplary polypeptides include gene products, naturally occurring proteins, homologs, orthologs, paralogs, fragments and other equivalents, variants, and analogs of the foregoing.

As used herein, the terms "ligand" and "binding molecule", and grammatical variants thereof, refer to a molecule or other chemical entity having a capacity for binding to a target. A ligand can comprise a peptide, an oligomer, a small molecule (e.g., a chemical compound), an antibody or fragment thereof, and/or any other affinity agent. In some embodiments, a ligand is a natural ligand of an EGFR family member such as EGF, TGFα, betacellulin, heparin-binding-EGF, epiregulin, or any other natural ligand for an ERBB family member. In some embodiments, a ligand is an artificial ligand such as an antibody or a small molecule that binds to an EGFR family member. In some embodiments, the phrase "binding molecules" refers to molecules (e.g. antibodies or small molecules) that modulate the activity of EGFR family members. In some embodiments, a binding molecule prevents signal transduction via an EGFR family member.

The term "binding" refers to an affinity between two molecules, for example, a ligand (e.g., a ligand of an EGFR family member, such as epidermal growth factor (EGF)) and a target (e.g., an EGFR family member). In some embodiments, the term "binding" refers to a specific binding of one molecule for another in a mixture of molecules. The binding of a ligand to a target molecule can be considered specific if the binding affinity is about $1 \times 10^4$ $M^{-1}$ to about $1 \times 10^6$ $M^{-1}$ or greater. For example, the binding of an antibody to an antigen can be thought of as having at least two components: an affinity, which refers to the strength at which the antibody binds an antigen, and a specificity, which refers to the level of cross-reactivity an antibody displays between closely related antigens.

The phrases "substantially lack binding" or "substantially no binding", as used herein to describe binding of a ligand in a control tissue, refers to a level of binding that encompasses non-specific or background binding, but does not include specific binding.

As used herein, the term "modulate", and grammatical variants thereof, refers to an increase, decrease, or other alteration of any or all biological activities or properties of an EGFR family member. Similarly, the term "modulator" refers to a compound (e.g. an antibody, antibody derivative, peptide, peptide mimetic, small molecule, polymer, etc.) that in some embodiments inhibits a biological activity of an EGFR family member. In these embodiments, the terms "EGFR modulator" and "EGFR inhibitor" are synonymous and are used interchangeably. "EGFR inhibitor" refers to a substance that acts by inhibiting, blocking, antagonizing, or otherwise reducing EGFR activity in cells and tissues.

The term "small molecule" as used herein refers to a compound, for example an organic compound, with a molecular weight in some embodiments of less than about 1,000 Daltons, in some embodiments less than about 750 Daltons, in some embodiments less than about 600 Daltons, and in some embodiments less than about 500 Daltons. In some embodiments, a small molecule also has a computed log octanol-water partition coefficient that in some embodiments is in the range of about −4 to about +14, and in some embodiments is in the range of about −2 to about +7.5.

As used herein, the term "obesity" means an increase in body weight beyond the limitation of skeletal and physical requirement, as the result of an excessive accumulation of adipose tissue in the body. One non-limiting quantitative definition of "obesity" or "obese", as used herein is a state in which a subject is at least about 5% over ideal body weight, including but not limited to at least about 10%, 15%, 20%, 30% or more above ideal body weight, wherein at least a portion of the excess body weight is excess adipose tissue. Another useful non-limiting quantitative definition of "obesity" or "obese", as used herein, is defined as having a body mass index (BMI) of 30 kg/m$^2$ or more (National Institutes of Health, Clinical Guidelines on the Identification, Evaluation, and Treatment of Overweight and Obesity in Adults (1998)). However, "obesity" or "obese" as used herein is also intended to include a disease, disorder, or condition that is characterized by a body mass index (BMI) of 25 kg/m$^2$ or more, 26 kg/m$^2$ or more, 27 kg/m$^2$ or more, 28 kg/m$^2$ or more, 29 kg/m$^2$ or more, kg/m$^2$ or more, or kg/m$^2$ or more, all of which are typically referred to as overweight (National Institute of Health, Clinical Guidelines on the Identification, Evaluation, and Treatment of Overweight and Obesity in Adults (1998)). Obesity is associated with and contributes to a variety of different disorders. (See, e.g., Nishina, P. M. et al. (1994), Metab. 43: 554-558; Grundy, S. M. & Barnett, J. P. (1990), Dis. Mon. 36: 641-731).

As used herein, the phrase "disorder associated with obesity" refers to any disease, disorder, and/or illness a symptom of which are associated with excess adipose tissue in the subject. Diseases that are associated with obesity are known to one of ordinary skill in the art. Exemplary, non-limiting disorders associated with obesity are heart disease, hypertension, stroke, Type II diabetes, arthritis, insulin resistance, atherosclerosis, coronary artery disease, hyperlipidemia (e.g., elevated circulating levels of cholesterol, triglycerides and lipoproteins), gallbladder disease, osteoarthritis, sleep apnea, liver cirrhosis, and cancer. It is to be understood that a subject need not necessarily be clinically obese in order to suffer from a disorder associated with obesity. These subjects and the disorders suffered by these subjects that are generally associated with obesity are intended to be included within the scope of the phrase "disorder associated with obesity".

II. Therapeutic Methods

The presently disclosed subject matter provides for the first time a correlation between modulation of one or more biological activities of EGFR and a reduction in the prevalence of obesity and disorders associated with obesity in subjects at risk for obesity. Accordingly, a method of treating or preventing obesity in a subject is provided. In some embodiments, the method comprises administering to the subject a treatment effective in reducing an activity of an EGFR in the subject, whereby obesity in the subject is treated or prevented. Additionally, a method of treating or preventing a disorder associated with obesity in a subject in need of such treatment is provided. In some embodiments, the method comprises administering to the subject a treatment effective in reducing an activity of an EGFR in the subject. In some embodiments, the disorder associated with obesity is selected from the group consisting of heart disease, hypertension, stroke, Type II diabetes, arthritis, insulin resistance, atherosclerosis, coronary artery disease, hyperlipidemia, gallbladder disease, osteoarthritis, sleep apnea, liver cirrhosis and cancer.

With reference to the therapeutic methods, a subject can be any subject in need of preventing or treating obesity and/or related disorders. For example, a subject that is already obese can be treated in order to reduce the subject's body weight by reducing excess adipose tissue, or even maintain a subject's body weight and prevent further significant adipose tissue deposition in the subject. For subjects treated to prevent obesity or disorders associated with obesity, the subject can be considered in need of such a treatment if, for example, the subject was predisposed to obesity or disorders associated with obesity. A subject can be considered predisposed for obesity or disorders associated with obesity if, for example, the subject had a genetic predisposition for obesity, or had at one time suffered from obesity and was at risk of becoming obese again.

A subject can be any vertebrate species. The methods of the presently disclosed subject matter are particularly useful in the treatment of warm-blooded vertebrates. Thus, the presently claimed subject matter concerns mammals. More particularly, provided is the treatment of mammals such as primates, including humans, as well as those mammals of importance due to being endangered (such as Siberian tigers), of economic importance (animals raised on farms for consumption by humans) and/or social importance to humans (animals kept as pets or in zoos), for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of disease in livestock, including, but not limited to domesticated swine (pigs and hogs), ruminants, horses, poultry, and the like.

II.A. EGFR Inhibitors

In some embodiments of the methods, the step of administering to the subject a treatment effective in reducing an activity of an EGFR in the subject comprises administering an effective amount of a composition comprising an EGFR binding molecule that reduces the activity of the EGFR. An EGFR activity can be any biological activity normally associated with an EGFR, including direct and indirect (secondary) activities of EGFR such as ligand binding (e.g., EGF and TGF binding), dimerization, kinase activity, signal transduction, and scaffolding activities (e.g., actin binding and molecule recruitment).

EGFR binding molecules of the presently disclosed subject matter include EGFR inhibitors. Representative EGFR inhibitors are known in the art (see e.g., Herbst et al., 2004, herein incorporated by reference) and include, for example, EGFR kinase inhibitors and antibodies having binding specificity for EGFR (i.e., anti-EGFR antibodies).

Exemplary EGFR kinase inhibitors include, but are not limited to IRESSA® (also known as gefitinib or ZD1839; AstraZeneca, London, United Kingdom), TARCEVA® (also known as erlotinib or OSI-774; OSI Pharmaceuticals, Inc., Melville, N.Y., U.S.A.), 4-(3-chloroanilino)-6,7-dimethoxyquinazoline (also known as AG 1478; A.G. Scientific, Inc., San Diego, Calif., U.S.A.), EKB-569 (Wyeth Pharmaceuticals, Collegeville, Pa., U.S.A.), EKI-785 (Wyeth Pharmaceuticals), PKI-166 (Novartis Pharmaceuticals, Basel, Switzerland), canertinib dihydrochloride (also known as CI-1033; Pfizer, Cambridge, Mass., U.S.A.), D-69491 (also known as SU11464; Baxter Oncology, Deerfield, Ill., U.S.A.), lapatinib ditosylate (also known as GW572016 or TYKERB®; GlaxoSmithKline, Middlesex, United Kingdom), ZD6474 (also known as ZACTIMA®; AstraZeneca, Sodertalje, Sweden), PKC-412 (Novartis Pharmaceuticals), sunitinib malate (also known as SUTENT® or SU-11248; Pfizer), vatalanib (also known as Ptk787/ZK222584), SU5614 (5-Chloro-3-[(3,5-dimethylpyrrol-2-yl)methylene]-2-indolinone; EMD Biosciences), CEP-701 (Cephalon, West Chester, Pa., U.S.A.), PKC-412 (Novartis Pharmaceuticals), MLN518 (Millennium Pharmaceuticals, Inc., Cambridge, Mass., U.S.A.), XL999 (Exelixis, Inc, San Francisco, Calif., U.S.A.), VX-322 (Vertex Pharmaceuticals, Inc., Cambridge, Mass., U.S.A.).

Anti-EGFR antibodies can be monoclonal or polyclonal antibodies. The antibodies can be chemically linked to another organic or biomolecule. Monoclonal and polyclonal antibodies can be made by any method generally known to those of ordinary skill in the art. (See, e.g., *Antibodies A Laboratory Manual*, E. Howell and D. Lane, Cold Spring Harbor Laboratory, 1988). For example, U.S. Pat. No. 5,422,245 to Nielsen et al. (assignee: Fonden Til Fremme AF Eksperimental Cancerforskning of Copenhagen, Denmark) describes the production of monoclonal antibodies to plasminogen activator inhibitor.

Briefly, a polyclonal antibody is prepared by immunizing an animal with an immunogen comprising a polypeptide or polynucleotide of the present subject matter (e.g., EGFR or a fragment thereof), and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

As is well known in the art, a given polypeptide or polynucleotide may vary in its immunogenicity. It is often necessary therefore to couple the immunogen (e.g., a polypeptide or polynucleotide) of the present invention) with a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers.

Means for conjugating a polypeptide or a polynucleotide to a carrier protein are well known in the art and include glutaraldehyde, m-maleimidobencoyl-N-hydroxysuccinimide ester, carbodiimide and bis-biazotized benzidine.

As is also well known in the art, immunogenicity to a particular immunogen can be enhanced by the use of non-specific stimulators of the immune response known as adjuvants. Exemplary and preferred adjuvants include complete Freund's adjuvant, incomplete Freund's adjuvants and aluminum hydroxide adjuvant.

The amount of immunogen used for the production of polyclonal antibodies varies, inter alia, upon the nature of the immunogen as well as the animal used for immunization. A variety of routes can be used to administer the immunogen, e.g. subcutaneous, intramuscular, intradermal, intravenous and intraperitoneal. The production of polyclonal antibodies is monitored by sampling blood of the immunized animal at various points following immunization. When a desired level of immunogenicity is obtained, the immunized animal can be bled and the serum isolated and stored.

A monoclonal antibody of the present subject matter can be readily prepared through use of well-known techniques such as those exemplified in U.S. Pat. No. 4,196,265, herein incorporated by reference. Typically, a technique involves first immunizing a suitable animal with a selected antigen (e.g., a polypeptide or polynucleotide of the present invention) in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is a murine NS-1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides. Where azaserine is used, the media is supplemented with hypoxanthine.

This culturing provides a population of hybridomas from which specific hybridomas are selected. Typically, selection of hybridomas is performed by culturing the cells by single-clone dilution in microtiter plates, followed by testing the individual clonal supernatants for reactivity with an antigen-polypeptides. The selected clones can then be propagated indefinitely to provide the monoclonal antibody.

By way of specific example, to produce an antibody of the present subject matter, mice are injected intraperitoneally with between about 1-200 μg of an antigen comprising a polypeptide of the presently disclosed subject matter. B lymphocyte cells are stimulated to grow by injecting the antigen in association with an adjuvant such as complete Freund's adjuvant (a non-specific stimulator of the immune response containing killed *Mycobacterium tuberculosis*). At some time (e.g., at least two weeks) after the first injection, mice are boosted by injection with a second dose of the antigen mixed with incomplete Freund's adjuvant.

A few weeks after the second injection, mice are tail bled and the sera titered by immunoprecipitation against radiolabeled antigen. Preferably, the method of boosting and titering is repeated until a suitable titer is achieved. The spleen of the mouse with the highest titer is removed and the spleen lymphocytes are obtained by homogenizing the spleen with a syringe. Typically, a spleen from an immunized mouse contains approximately $5 \times 10^7$ to $2 \times 10^8$ lymphocytes.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells are tumor cells, they can be propagated indefinitely in tissue culture, and are thus denominated immortal. Numerous cultured cell lines of myeloma cells from mice and rats, such as murine NS-1 myeloma cells, have been established.

Myeloma cells are combined under conditions appropriate to foster fusion with the normal antibody-producing cells from the spleen of the mouse or rat injected with the antigen/polypeptide of the present invention. Fusion conditions include, for example, the presence of polyethylene glycol. The resulting fused cells are hybridoma cells. Like myeloma cells, hybridoma cells grow indefinitely in culture.

Hybridoma cells are separated from unfused myeloma cells by culturing in a selection medium such as HAT media (hypoxanthine, aminopterin, thymidine). Unfused myeloma cells lack the enzymes necessary to synthesize nucleotides from the salvage pathway because they are killed in the presence of aminopterin, methotrexate, or azaserine. Unfused lymphocytes also do not continue to grow in tissue culture. Thus, only cells that have successfully fused (hybridoma cells) can grow in the selection media.

Each of the surviving hybridoma cells produces a single antibody. These cells are then screened for the production of the specific antibody immunoreactive with an antigen/polypeptide of the present subject matter. Single cell hybridomas are isolated by limiting dilutions of the hybridomas. The hybridomas are serially diluted many times and, after the dilutions are allowed to grow, the supernatant is tested for the presence of the monoclonal antibody. The clones producing that antibody are then cultured in large amounts to produce an antibody of the presently disclosed subject matter in convenient quantity.

By use of a monoclonal antibody of the presently disclosed subject matter, specific polypeptides and polynucleotide of the present subject matter can be recognized as antigens, and thus identified. Once identified, those polypeptides and polynucleotide can be isolated and purified by techniques such as antibody-affinity chromatography. In antibody-affinity chromatography, a monoclonal antibody is bound to a solid substrate and exposed to a solution containing the desired antigen. The antigen is removed from the solution through an immunospecific reaction with the bound antibody. The polypeptide or polynucleotide is then easily removed from the substrate and purified.

Exemplary anti-EGFR antibodies presently available for use with the therapeutic methods disclosed herein include, but are not limited to ERBITUX® (also known as cetuximab or IMC-C225; Goldstein et al., 1995; Imclone Systems, Inc., New York, N.Y., U.S.A.), ABX-EGF (Abgenix, Fremont, Calif., U.S.A.), HERCEPTIN® (also known as trastuzumab; Genentech, Inc., San Francisco, Calif., U.S.A.), and EMD 72000 (also known as maztuzumab; EMD Pharmaceuticals, Durham, N.C., U.S.A.).

II.B. Modulation of EGFR Expression

In some embodiments of the therapeutic methods, the step of administering to the subject a treatment effective in reducing an activity of an EGFR in the subject comprises administering an effective amount of a composition that modulates expression of the EGFR in the subject. Modulating expression of the EGFR can comprise in some embodiments modulating transcription and/or translation of the EGFR in one or more cells or tissues of the subject.

In accordance with the presently disclosed subject matter, the composition can optionally comprise an antibody or polypeptide which transcriptionally modulates expression of EGFR. Optionally, the antibody or polypeptide directly binds to DNA or RNA, or directly binds to a protein involved in transcription.

Representative chemical entities (e.g., small molecule mimetics) for use in accordance with the presently disclosed subject matter do not naturally occur in any cell, whether of a multicellular or a unicellular organism. In some embodiments the chemical entity is not a naturally occurring molecule, e.g., it is a chemically synthesized entity. Optionally, the compound can bind a modulatable transcription sequence of the gene. For example, the compound can bind a promoter region upstream of a nucleic acid sequence encoding an EGFR.

In the methods above, modulation of transcription results in either upregulation or downregulation of expression of the gene encoding the protein of interest, depending on the identity of the molecule that contacts the cell.

Expression can also be modulated in a subject through the administration of an antisense oligonucleotide derived from a nucleic acid molecule encoding an EGFR, such as for example the nucleic acid molecules disclosed in Table 1. Therapeutic methods utilizing antisense oligonucleotides have been described in the art, for example, in U.S. Pat. Nos. 5,627,158 and 5,734,033, the contents of each of which are herein incorporated by reference. Exemplary antisense oligonucleotides include small interfering RNAs (siRNA).

The term "RNA" refers to a molecule comprising at least one ribonucleotide residue. By "ribonucleotide" is meant a nucleotide with a hydroxyl group at the 2' position of a β-D-ribofuranose moiety. The terms encompass double stranded RNA, single stranded RNA, RNAs with both double stranded and single stranded regions, isolated RNA such as partially purified RNA, essentially pure RNA, synthetic RNA, recombinantly produced RNA, as well as altered RNA, or analog RNA, that differs from naturally occurring RNA by the addition, deletion, substitution, and/or alteration of one or more nucleotides. Such alterations can include addition of non-nucleotide material, such as to the end(s) of an siRNA or internally, for example at one or more nucleotides of the RNA. Nucleotides in the RNA molecules of the presently disclosed subject matter can also comprise non-standard nucleotides, such as non-naturally occurring nucleotides or chemically synthesized nucleotides or deoxynucleotides. These altered RNAs can be referred to as analogs or analogs of a naturally occurring RNA.

The terms "small interfering RNA", "short interfering RNA", "small hairpin RNA", "siRNA", and shRNA are used interchangeably and refer to any nucleic acid molecule capable of mediating RNA interference (RNAi) or gene silencing. See e.g., Bass, Nature 411:428-429, 2001; Elbashir et al., Nature 411:494-498, 2001a; and PCT International Publication Nos. WO 00/44895, WO 01/36646, WO 99/32619, WO 00/01846, WO 01/29058, WO 99/07409, and WO 00/44914. In one embodiment, the siRNA comprises a double stranded polynucleotide molecule comprising complementary sense and antisense regions, wherein the antisense region comprises a sequence complementary to a region of a target nucleic acid molecule (for example, a nucleic acid molecule encoding an EGFR). In another embodiment, the siRNA comprises a single stranded polynucleotide having self-complementary sense and antisense regions, wherein the antisense region comprises a sequence complementary to a region of a target nucleic acid molecule. In another embodiment, the siRNA comprises a single stranded polynucleotide having one or more loop structures and a stem comprising self complementary sense and antisense regions, wherein the antisense region comprises a sequence complementary to a region of a target nucleic acid molecule, and wherein the polynucleotide can be processed either in vivo or in vitro to generate an active siRNA capable of mediating RNAi. As used herein, siRNA molecules need not be limited to those molecules containing only RNA, but further encompass chemically modified nucleotides and non-nucleotides.

The presently disclosed subject matter takes advantage of the ability of short, double stranded RNA molecules to cause the down regulation of cellular genes, a process referred to as RNA interference. As used herein, "RNA interference" refers to a process of sequence-specific post-transcriptional gene silencing mediated by a small interfering RNA (siRNA). See generally Fire et al., Nature 391:806-811, 1998. The process of post-transcriptional gene silencing is thought to be an evolutionarily conserved cellular defense mechanism that has evolved to prevent the expression of foreign genes (Fire, Trends Genet. 15:358-363, 1999).

RNAi might have evolved to protect cells and organisms against the production of double stranded RNA (dsRNA) molecules resulting from infection by certain viruses (particularly the double stranded RNA viruses or those viruses for which the life cycle includes a double stranded RNA intermediate) or the random integration of transposon elements into the host genome via a mechanism that specifically degrades single stranded RNA or viral genomic RNA homologous to the double stranded RNA species.

The presence of long dsRNAs in cells stimulates the activity of the enzyme Dicer, a ribonuclease III. Dicer catalyzes the degradation of dsRNA into short stretches of dsRNA referred to as small interfering RNAs (siRNA) (Bernstein et al., Nature 409:363-366, 2001). The small interfering RNAs that result from Dicer-mediated degradation are typically about 21-23 nucleotides in length and contain about 19 base pair duplexes. After degradation, the siRNA is incorporated into an endonuclease complex referred to as an RNA-induced silencing complex (RISC). The RISC is capable of mediating cleavage of single stranded RNA present within the cell that is complementary to the antisense strand of the siRNA duplex. According to Elbashir et al., cleavage of the target RNA occurs near the middle of the region of the single stranded RNA that is complementary to the antisense strand of the siRNA duplex (Elbashir et al., Genes Dev 15:188-200, 2001b).

RNAi has been described in several cell type and organisms. Fire et al., 1998 described RNAi in C. elegans. Wianny & Zernicka-Goetz, Nature Cell Biol 2:70-75, 1999 disclose RNAi mediated by dsRNA in mouse embryos. Hammond et al., Nature 404:293-296, 2000 were able to induce RNAi in Drosophila cells by transfecting dsRNA into these cells. Elbashir et al. Nature 411:494-498, 2001a demonstrated the presence of RNAi in cultured mammalian cells including human embryonic kidney and HeLa cells by the introduction of duplexes of synthetic 21 nucleotide RNAs.

Other studies have indicated that a 5'-phosphate on the target-complementary strand of a siRNA duplex facilitate siRNA activity and that ATP is utilized to maintain the 5'-phosphate moiety on the siRNA (Nykanen et al., Cell 107: 309-321, 2001). Other modifications that might be tolerated when introduced into an siRNA molecule include modifications of the sugar-phosphate backbone or the substitution of the nucleoside with at least one of a nitrogen or sulfur heteroatom (PCT International Publication Nos. WO 00/44914 and WO 01/68836) and certain nucleotide modifications that might inhibit the activation of double stranded RNA-dependent protein kinase (PKR), specifically 2'-amino or 2'-O-methyl nucleotides, and nucleotides containing a 2'-O or 4'-C methylene bridge (Canadian Patent Application No. 2,359, 180).

Other references disclosing the use of dsRNA and RNAi include PCT International Publication Nos. WO 01/75164 (in vitro RNAi system using cells from Drosophila and the use of specific siRNA molecules for certain functional genomic and certain therapeutic applications); WO 01/36646 (methods for inhibiting the expression of particular genes in mammalian cells using dsRNA molecules); WO 99/32619 (methods for introducing dsRNA molecules into cells for use in inhibiting gene expression); WO 01/92513 (methods for mediating gene suppression by using factors that enhance RNAi); WO 02/44321 (synthetic siRNA constructs); WO 00/63364 and WO 01/04313 (methods and compositions for inhibiting the function of polynucleotide sequences); and WO 02/055692 and WO 02/055693 (methods for inhibiting gene expression using RNAi).

In some embodiments, the presently disclosed subject matter utilizes RNAi to at least partially inhibit expression of at least one EGFR. Inhibition is preferably at least about 10% of normal expression amounts. In some embodiments, the method comprises introducing an RNA to a target cell in an amount sufficient to inhibit expression of an EGFR, wherein the RNA comprises a ribonucleotide sequence which corresponds to a coding strand of a gene of interest. In some embodiments, the target cell is present in a subject, and the RNA is introduced into the subject.

The RNA can have a double-stranded region comprising a first strand comprising a ribonucleotide sequence that corresponds to the coding strand of the gene encoding the target protein (for example, an EGFR) and a second strand comprising a ribonucleotide sequence that is complementary to the first strand. The first strand and the second strand hybridize to each other to form the double-stranded molecule. The double stranded region can be at least 15 basepairs in length, and in some embodiments, between 15 and 50 basepairs in length, and in some embodiments the double stranded region is between 15 and 30 basepairs in length.

In some embodiments, the RNA comprises one strand that forms a double-stranded region by intramolecular self-hybridization, which is preferably complementary over at least 19 bases. In some embodiments, the RNA comprises two separate strands that form a double-stranded region by intermolecular hybridization that is complementary over at least 19 bases.

One skilled in the art will recognize that any number of suitable common techniques can be used to introduce the RNAs into a target cell. In some embodiments, a vector encoding the RNA is introduced to the target cell. For example, the vector encoding the RNA can be transfected into the target cell and the RNA is then transcribed by cellular polymerases.

In some embodiments, a recombinant virus comprising nucleic acid encoding the RNA can be produced. Introducing the RNA into a target cell then comprises infecting the target cell with the recombinant virus. Cellular polymerases transcribe the RNA resulting in expression of the RNA within the target cell. Engineering recombinant viruses is well known to those having ordinary skill in the art. One of skill would readily appreciate the multiple factors involved in selecting the appropriate virus and vector components needed to optimize recombinant virus production for use with the presently disclosed subject matter without the necessity of further detailed discussion herein. As one non-limiting example, a recombinant adenovirus can be engineered comprising DNA encoding an siRNA. The virus can be engineered to be replication deficient such that cells can be infected by the recombinant adenovirus, the siRNA transcribed, and transiently expressed in the infected target cell. Details of recombinant virus production and use can be found in published PCT Patent Application No. PCT/US02/22010, herein incorporated by reference in their entireties. Alternatively, a commercial kit for producing recombinant viruses can be used, such as for example, the pSILENCER ADENO 1.0-CMV SYSTEM™ (Ambion, Austin, Tex., U.S.A.).

II.C Formulation of Therapeutic Compositions

The EGFR biological activity modulating substances, including EGFR expression-modulating compositions (e.g., antisense oligonucleotides) and substances that bind and modulate EGFR activities, and prodrugs and pharmaceutical salts thereof can be adapted for administration as a pharmaceutical composition. Additional formulation and dose preparation techniques have been described in the art (see e.g., those described in U.S. Pat. No. 5,326,902 issued to Seipp et al. on Jul. 5, 1994; U.S. Pat. No. 5,234,933 issued to Marnett et al. on Aug. 10, 1993; and PCT International Publication Number WO 93/25521 of Johnson et al., published Dec. 23, 1993, the entire contents of each of which are herein incorporated by reference).

For therapeutic applications, a treatment effective amount of a composition of the presently disclosed subject matter is administered to a subject. A "treatment effective amount" or "effective amount" is an amount of the therapeutic composition sufficient to produce a measurable biological response, such as but not limited to a reduction in a EGFR biological activity. Actual dosage levels of active ingredients in a therapeutic composition of the presently disclosed subject matter can be varied so as to administer an amount of the active compound(s) that is effective to achieve the desired therapeutic response for a particular subject. The selected dosage level will depend upon a variety of factors including, but not limited to the activity of the therapeutic composition, the formulation, the route of administration, combinations with other drugs or treatments, and the physical condition and prior medical history of the subject being treated. In some embodiments, a minimal dose is administered, and the dose is escalated in the absence of dose-limiting toxicity. The determination and adjustment of a therapeutically effective dose, as well as evaluation of when and how to make such adjustments, are well known to those of ordinary skill in the art of medicine. Further, the therapeutic compositions disclosed herein can be administered alone, or in combination with other therapies (e.g., diet regimens and exercise) and/or therapeutics.

For the purposes described above, the identified substances can normally be administered systemically or partially, usually by oral or parenteral administration. The doses to be administered are determined depending upon age, body weight, symptom, the desired therapeutic effect, the route of administration, and the duration of treatment, etc.; one of skill in the art of therapeutic treatment will recognize appropriate procedures and techniques for determining the appropriate dosage regimen for effective therapy. Various compositions and forms of administration are provided and are generally known in the art. Other compositions for administration include liquids for external use, and endermic liniments (ointment, etc.), suppositories, and pessaries that comprise one or more of the active substance(s) and can be prepared by known methods.

Thus, the presently disclosed subject matter provides pharmaceutical compositions comprising in some embodiments a polypeptide, polynucleotide, antibody or fragment thereof, small molecule, or compound of the presently disclosed subject matter, and a physiologically acceptable carrier. In some embodiments, a pharmaceutical composition comprises a compound discovered via the screening methods described herein.

A composition of the presently disclosed subject matter is typically administered parenterally in dosage unit formulations containing standard, well-known nontoxic physiologically acceptable carriers, adjuvants, and vehicles as desired. The term "parenteral" as used herein includes, but is not limited to intravenous, intramuscular, intra-arterial injection, or infusion techniques.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable carriers and solvents that can be employed are water, Ringer's solution, and isotonic sodium chloride solution. In addition, sterile, fixed oils are conventionally employed as solvents or suspending media. For this purpose, any bland fixed oil can be employed including synthetic mono- or diglycerides. In addition, fatty acids such as oleic acid find use in the preparation of injectables.

Representative, non-limiting carriers include neutral saline solutions buffered with phosphate, lactate, Tris, and the like. Of course, one purifies the carrier sufficiently to render it essentially free of undesirable contaminants such that it does not cause any untoward reactions in the individual receiving the carrier and therapeutic composition(s).

A transfected cell can also serve as a carrier. By way of example, a liver cell can be removed from an organism, transfected with a polynucleotide of the presently disclosed subject matter using methods known to one of skill in the art, and then the transfected cell returned to the organism (e.g., injected intra-vascularly).

Additionally, therapeutic compositions described herein can be administered as pharmaceutically acceptable salts. Such pharmaceutically acceptable salts include the gluconate, lactate, acetate, tartarate, citrate, phosphate, maleate, borate, nitrate, sulfate, and hydrochloride salts. The salts of the compounds described herein can be prepared, for example, by reacting the base compound with the desired acid in solution. After the reaction is complete, the salts are crystallized from solution by the addition of an appropriate amount of solvent in which the salt is insoluble.

III. Screening Assays

In yet another aspect, the presently disclosed subject matter provides a method of screening substances for their ability to affect or modulate a biological activity of Egfr family gene products associated with obesity. Utilizing the methods and compositions of the present subject matter, screening assays for the testing of candidate substances can be derived. A candidate substance is a substance which potentially can modulate a biological activity associated with obesity of an Egfr family gene product by binding, or other intermolecular interaction, with the Egfr family gene product.

An exemplary method of screening candidate substances for their ability to modulate an activity of an EGFR associated with obesity comprises the steps of: (a) establishing replicate test and control samples that comprise a biologically active EGFR polypeptide associated with obesity; (b) administering a candidate substance to the test sample but not the control sample; (c) measuring the biological activity of the EGFR polypeptide in the test and the control samples; and (d) determining that the candidate substance modulates EGFR biological activity if the biological activity of the EGFR polypeptide measured for the test sample is greater or less than the biological activity of the EGFR polypeptide measured for the control sample. The biological activities associated with obesity that can be examined in connection with a screening assay of the present subject matter comprise modulating kinase activity, ligand binding, signal transduction and/or scaffolding functions of the EGFR polypeptide in accordance with the presently disclosed subject matter.

The term "candidate composition", as used herein, refers to any molecule, e.g., a protein or small molecule, with the capability of affecting a molecular and/or clinical phenomena associated with EGFR activity. Generally, pluralities of assay mixtures are run in parallel with different candidate composition concentrations to obtain a differential response to the various concentrations. Typically, one of these concentrations serves as a negative control (i.e., at zero concentration or below the level of detection).

Candidate compositions can encompass numerous chemical classes, though typically they are organic molecules, in some embodiments small organic compounds having a molecular weight of more than 50 and less than about 2,500 Daltons. Candidate compositions can comprise functional groups necessary for structural interaction with proteins, particularly hydrogen bonding, and typically include at least an amine, carbonyl, hydroxyl or carboxyl group, and sometimes at least two of the functional chemical groups. The candidate compositions often comprise cyclical carbon or heterocyclic structures and/or aromatic or polyaromatic structures substituted with one or more of the above functional groups. Candidate compositions are also found among biomolecules including, but not limited to peptides, saccharides, fatty acids, steroids, purines, pyrimidines, derivatives and structural analogs thereof, and combinations thereof.

Candidate compositions can be obtained from a wide variety of sources including libraries of synthetic or natural compounds. For example, numerous approaches are available for random and directed synthesis of a wide variety of organic compounds and biomolecules, including expression of randomized oligonucleotides and oligopeptides. Alternatively, libraries of natural compounds in the form of bacterial, fungal, plant, and animal extracts are available or can be readily produced. Additionally, natural or synthetically produced libraries and compounds can be readily modified through conventional chemical, physical, and biochemical approaches, and can be used to produce combinatorial libraries. Known pharmacological agents can be subjected to directed or random chemical modifications, such as acylation, alkylation, esterification, amidification, etc., to produce structural analogs.

The replicate test and control samples can further comprise a cell that expresses a biologically active EGFR polypeptide. The presently disclosed subject matter also provides a recombinant cell line suitable for use in the exemplary method. A candidate substance identified according to the screening assay described herein can have the ability to modulate EGFR biological activity (e.g., EGFR kinase activity). Such a candidate compound has utility in the treatment or prevention of obesity and disorders associated with obesity.

In a cell-free system, the method comprises the steps of establishing a control system comprising an EGFR polypeptide and a ligand wherein the EGFR polypeptide is capable of binding to the ligand; establishing a test system comprising the EGFR polypeptide, the ligand, and a candidate compound; measuring the binding affinity of the EGFR polypeptide and the ligand in the control and the test systems; and determining that the candidate compound modulates EGFR activity in a cell-free system if the binding affinity measured for the test system is less than or greater than the binding affinity measured for the control system.

As is well known in the art, a screening assay provides a cell under conditions suitable for testing the modulation of an EGFR biological activity. These conditions include but are not limited to pH, temperature, tonicity, the presence of relevant metabolic factors (e.g., metal ions such as for example $Ca^{++}$, growth factor, interleukins, or colony stimulating factors), and relevant modifications to the polypeptide such as phosphorylation, glycosylation or prenylation. A polypeptide of the present subject matter can be expressed and utilized in a prokaryotic or a eukaryotic cell. The host cell can also be fractionated into sub-cellular fractions where the receptor can be found. For example, cells expressing the polypeptide can be fractionated into the nuclei, the endoplasmic reticulum, vesicles, or the membrane surfaces of the cell.

In a preferred embodiment, temperature is from about 20° C. to about 50° C., more preferably from about 30° C. to about 40° C. and, even more preferably about 37° C. Osmolality is preferably from about 5 milliosmols per liter (mosm/L) to about 400 mosm/l and, more preferably from about 200 milliosmols per liter to about 400 mosm/l and, even more preferably from about 290 mosm/L to about 310 mosm/L. The presence of factors can be required for the proper testing of EGFR biological activity modulation in specific cells. Such factors include, for example, the presence and absence (withdrawal) of growth factor, interleukins, or colony stimulating factors. U.S. Pat. Nos. 5,837,479; 5,645,999; 5,786,152; 5,739,278; and 5,352,660 also describe exemplary screening assays, and the entire contents of each are herein incorporated by reference.

In some embodiments, the replicate test and control samples are replicate test and control animals. Further, in these embodiments, the EGFR biological activity can be measured by measuring a change in the amount of adipose tissue in the test and control animals over time after treatment (test animals) with the candidate substance. Less of an increase in adipose tissue in test animals as compared to control animals can be indicative of the candidate substance having an ability to inhibit an EGFR biological activity associated with obesity.

EXAMPLES

The following Examples have been included to illustrate modes of the presently disclosed subject matter. In light of the present disclosure and the general level of skill in the art, those of skill will appreciate that the following Examples are intended to be exemplary only and that numerous changes, modifications, and alterations can be employed without departing from the scope of the presently disclosed subject matter.

Materials and Methods for Examples 1-6

Diets: A base Western Diet (D12079B, Research Diets, Inc., New Brunswick, N.J., U.S.A.) having 41% fat (kcal) was used in all studies, and is designated HFD. The small molecule inhibitor AG1478 (LC Laboratories, Woburn, Mass., U.S.A.) was added to this base diet to a final concentration of 114 ppm. This diet is designated HFD+INH.

Mouse Models of Reduced Egfr Activity:

Genetic Models

The waved-2 hypomorphic mutation in the ATP binding domain of the EGFR results in up to 90% reduction in EGFR activity in mice homozygous for this mutation. To determine if genetic reduction of EGFR activity affected weight gain, 12-20 week-old male and female Egfr wa2/wa2 and Egfr wa2/+ littermates from B6 and 129S6/SvEv (129S6) Egfr wa2 congenic lines were housed together and placed on the HFD for up to 3 months.

A Cre-LoxP strategy was used to specifically reduce or ablate EGFR activity in selected organ systems. Egfr flox/flox mice having LoxP sites flanking exon 3 of the EGFR gene were created and bred to two established transgenic Cre lines (Villin-Cre and GFAP Cre). In these transgenic lines, Cre recombinase is expressed primarily in intestine and CNS, respectively, under the control of specific promoters. To determine if reduced EGFR activity in these organ systems impacted weight gain, 12-14 week-old male and female littermates from Egfr flox/flox×Egfr flox/+Cre or Egfr flox/flox×Egfr flox/flox Cre matings were housed together and placed on the HFD for up to three months.

Pharmaceutical Model

In experiments using wild-type C57BL6/J (B6) mice, male mice were housed individually and were started on the diet experiments at 8 weeks of age. In Example 2, mice were maintained on the HFD or HFD+INH for 1 month. In Example 3, mice were maintained on the HFD (n=8) or HFD+INH (n=8) for 6 months. In Example 4, all mice were placed on the HFD for 3 months; after this time, Group 1 (n=4) was placed on HFD+INH, while Group 2 (n=4) was maintained on HFD.

Clinical chemistry: Non-fasted blood glucose levels were measured at baseline and monthly using the FREESTYLE® blood glucose monitor (Abbott Laboratories, Abbott Park, Ill., U.S.A.) which was calibrated per manufacturer's instruction prior to use. All measurements were taken from 4-5 pm. At sacrifice, blood was collected by retro-orbital bleed and serum was isolated. Serum concentrations of triglycerides and total cholesterol were measured using an automatic blood chemical analyzer (Johnson & Johnson, New Brunswick, N.J., U.S.A.) by the University of North Carolina at Chapel Hill Animal Clinical Chemistry and Gene Expression Laboratories Core.

Body composition analysis: On the day of analysis, mice were weighed, anaesthetized with 2-3% isofluorane, and body composition was determined with a PIXIMUS II™ Mouse Densitometer (GE Medical Systems, distributed by Faxitron X-Ray Corporation, Wheeling, Ill., U.S.A.) using software versions 1.46 and 2.10. These measurements were taken at baseline and monthly during the diet studies. The Dual-energy X-ray absorptiometry (DEXA) method of determining body composition and body fat has been validated in lean and obese mice (Brommage (2003) J Physiol Endocrinol Metab 285: E454-459).

Statistical analysis: Results are expressed as mean+/−STD. A two-sided unpaired student's t-test was used for preliminary statistical analysis.

Example 1

The effect on adipose tissue accumulation in wild-type and EGFR mutant mice fed a high fat diet (HFD) was investigated. Wild-type mice and mice homozygous for the hypomorphic Egfr waved-2 allele ($Egfr^{wa2/wa2}$; Luetteke et al., 1994) were fed a high fat diet for up to about three (3) months. The $Egfr^{wa2}$ allele contains a single nucleotide mutation producing a valine to glycine amino acid substitution in the kinase domain, resulting in up to a 90% reduction in kinase activity. The wild-type mice were considerably heavier, and body scans revealed that the cause of this substantial weight gain was an increase in adipose tissue accumulation. This increase in adipose tissue accumulation was accompanied by an increase in blood glucose levels.

These results are disclosed below and in FIGS. 1-8. As can be seen therein, the presence of a wild-type Egfr results in significant weight gains in mice fed a high fat diet, while the absence of wild-type Egfr substantially inhibits this outcome. These effects were seen in mice from two different strains, suggesting that the weight gain and blood glucose increases are not the result of a strain-specific phenomenon.

FIG. 1 shows weight gains experienced by wild-type (wt) C57BL/6 mice and mice from a C57BL/6 background that were either heterozygous (wa2/+) or homozygous (wa2/wa2) for the wa2 allele of Egfr. For each grouping, the left data point depicts the average weight in grams of the mice in the group at the initiation of feeding with the high fat diet (baseline at day 0; light gray), and the right data point depicts the average weight in grams of the mice in the group after about four (4) weeks on the high fat diet. Also included are error bars depicting two (2) standard deviations for each result.

FIGS. 2A and 2B show body scans of a representative C57BL/6 wild-type mouse (FIG. 2A) and a representative $Egfr^{wa2/wa2}$ C57BL/6 mouse (FIG. 2B) after about four (4) weeks on the high fat diet. As can be seen, the wild-type mouse has considerable adipose tissue accumulation, while the $Egfr^{wa2/wa2}$ mouse does not.

FIGS. 3-6 depict body weight and blood glucose assays of C57BL/6 and 129 strain male and female mice that are heterozygous or homozygous for a wa2 allele exposed to a high fat diet (HFD; 45% kcal from fat) for up to about 3 months. The mice were approximately 3-4 months old when started on the dietary study. For each of FIGS. 3-6, solid squares (■) correspond to heterozygous male mice, solid circles (●) correspond to heterozygous female mice, open squares (□) correspond to homozygous male wa2 mice, and open circles (○) correspond to homozygous female wa2 mice. Each Figure also includes error bars equal to ±2 standard deviations.

Figure 3:
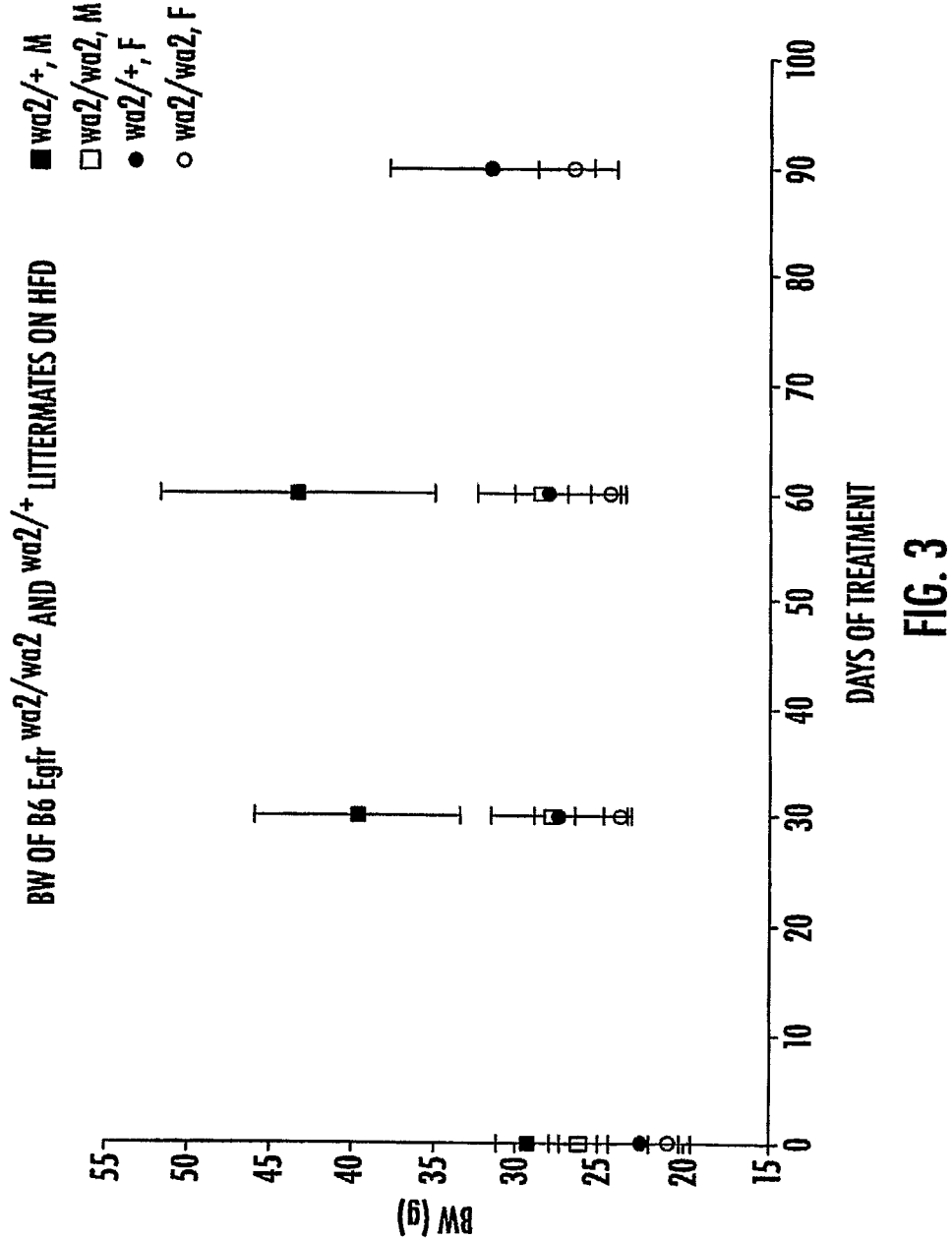
FIG. 3 is a graph depicting body weight measurements of heterozygous and homozygous wa2 mice on a C57BL/6 background fed a high fat diet for up to about 3 months. Solid squares (■) correspond to heterozygous male mice, solid circles (●) correspond to heterozygous female mice, open squares (□) correspond to homozygous male wa2 mice, and open circles (○) correspond to homozygous female wa2 mice.

FIG. 3 depicts body weight measurements of heterozygous and homozygous wa2 mice on a C57BL/6 background fed a high fat diet for up to about 3 months. The data include measurements of 7 heterozygous male mice at days 0, 30, and 60; 10 heterozygous female mice at days 0, 30, 60, and 90; and 6 homozygous female mice at days 0, 30, 60, and 90. For the homozygous male mice, 3 mice were measured at day 0, 5 mice were measured at day 30, 3 mice were measured at day 60, and 0 mice were measured at day 90, due to the death of the test mice over the 3 month period, presumably from cardiac hypertrophy secondary to aortic valve defects. Statistics based on the Wilcoxon rank sum test were used to compare heterozygous mice to homozygous mice at each time point, with males being compared to males and females to females. The results of the statistical analysis are as follows: baseline: $p<0.02$ males; 30 days: $p<0.008$ males; 60 days: $p<0.09$ males, $p<0.09$ females; 90 days: $p<0.09$ females.

Figure 4:
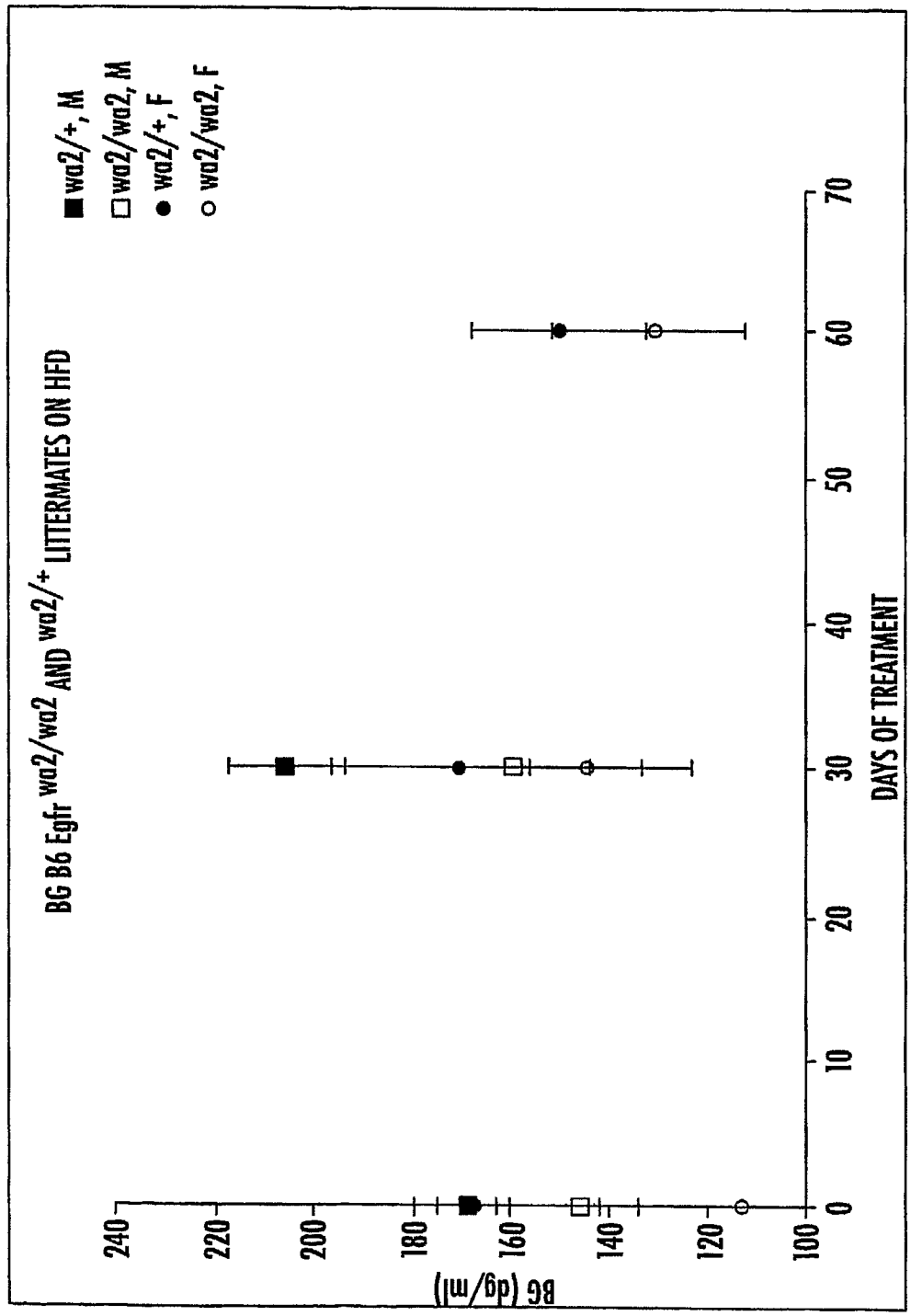
FIG. 4 is a graph depicting blood glucose levels of heterozygous and homozygous wa2 mice on a C57BL/6 background fed a high fat diet for up to about 2 months. Solid squares (■) correspond to heterozygous male mice, solid circles (●) correspond to heterozygous female mice, open squares (□) correspond to homozygous male wa2 mice, and open circles (○) correspond to homozygous female wa2 mice.

FIG. 4 depicts blood glucose levels of heterozygous and homozygous wa2 mice on a C57BL/6 background fed a high fat diet for up to about 2 months. The data include measurements of 7 heterozygous male mice at days 0 and 30; 4 homozygous male mice at days 0 and 30; 7 heterozygous female mice at days 0, 30, and 60; and 6 homozygous female mice at days 0, 30, and 60. Statistics based on the Wilcoxon rank sum test were calculated as described with respect to the data shown in FIG. 3. The results of the statistical analysis are as follows: baseline: $p<0.02$ males and $p<0.04$ females; 30 days: $p<0.10$ males and $p<0.04$ females; 60 days: $p<0.10$ males, $p<0.14$ females.

Figure 5:
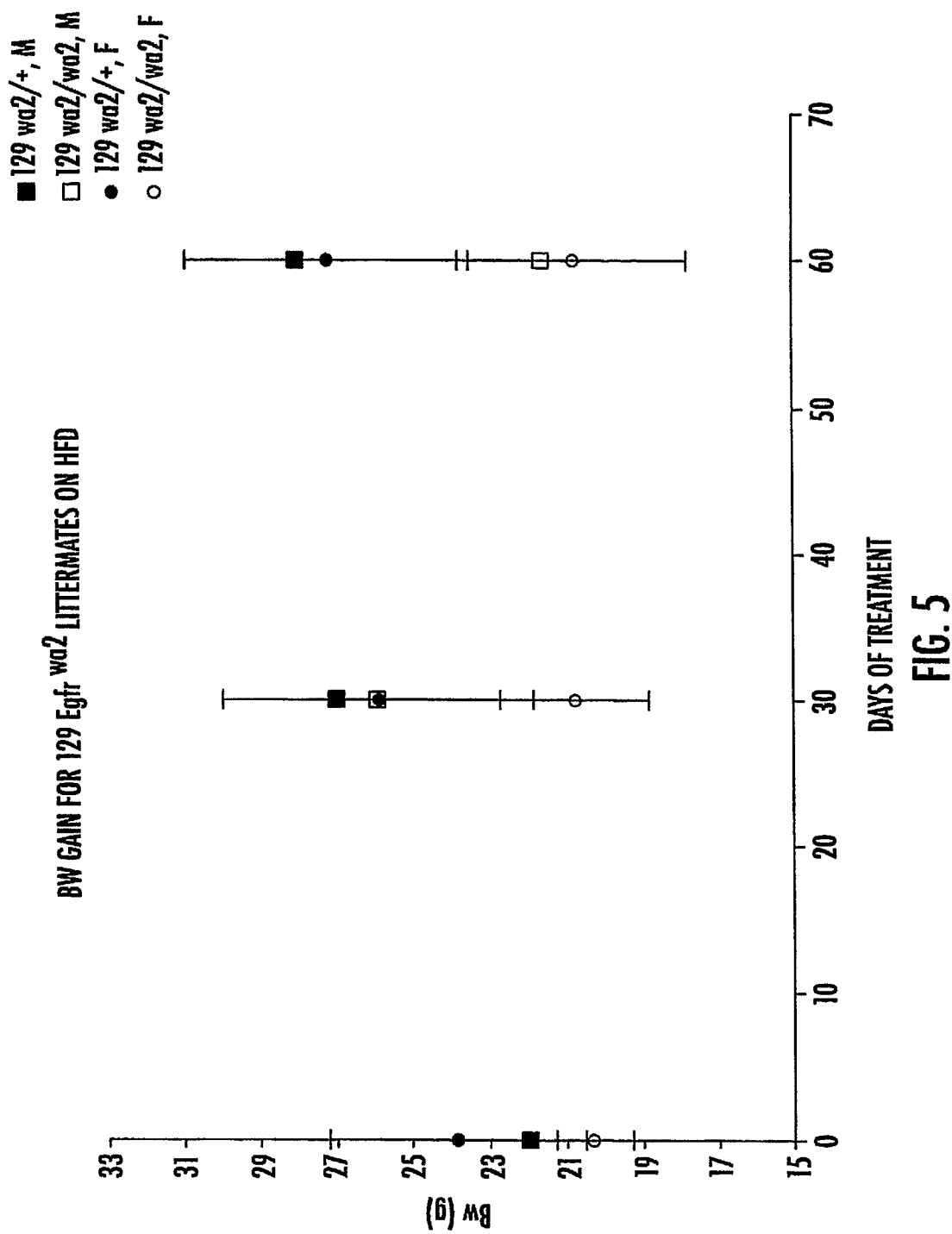
FIG. 5 is a graph depicting body weight measurements of heterozygous and homozygous wa2 mice on a 129 background fed a high fat diet for up to about 3 months. Solid squares (■) correspond to heterozygous male mice, solid circles (●) correspond to heterozygous female mice, open squares (□) correspond to homozygous male wa2 mice, and open circles (○) correspond to homozygous female wa2 mice.

FIG. 5 depicts body weight measurements of heterozygous and homozygous wa2 mice on a 129 background fed a high fat diet for up to about 3 months. The data include measurements of 2 heterozygous male mice at days 0, 30, and 60; 1 homozygous male mouse at days 0, 30, and 60; 10 heterozygous female mice at days 0, 30, and 60; and 6 homozygous female mice at days 0, 30, and 60. Statistics based on the Wilcoxon rank sum test were calculated as described with respect to the data shown in FIG. 3. The results of the statistical analysis are as follows: baseline: $p<0.10$ females; 30 days: $p<0.06$ females; 60 days: $p<0.03$ females.

Figure 6:
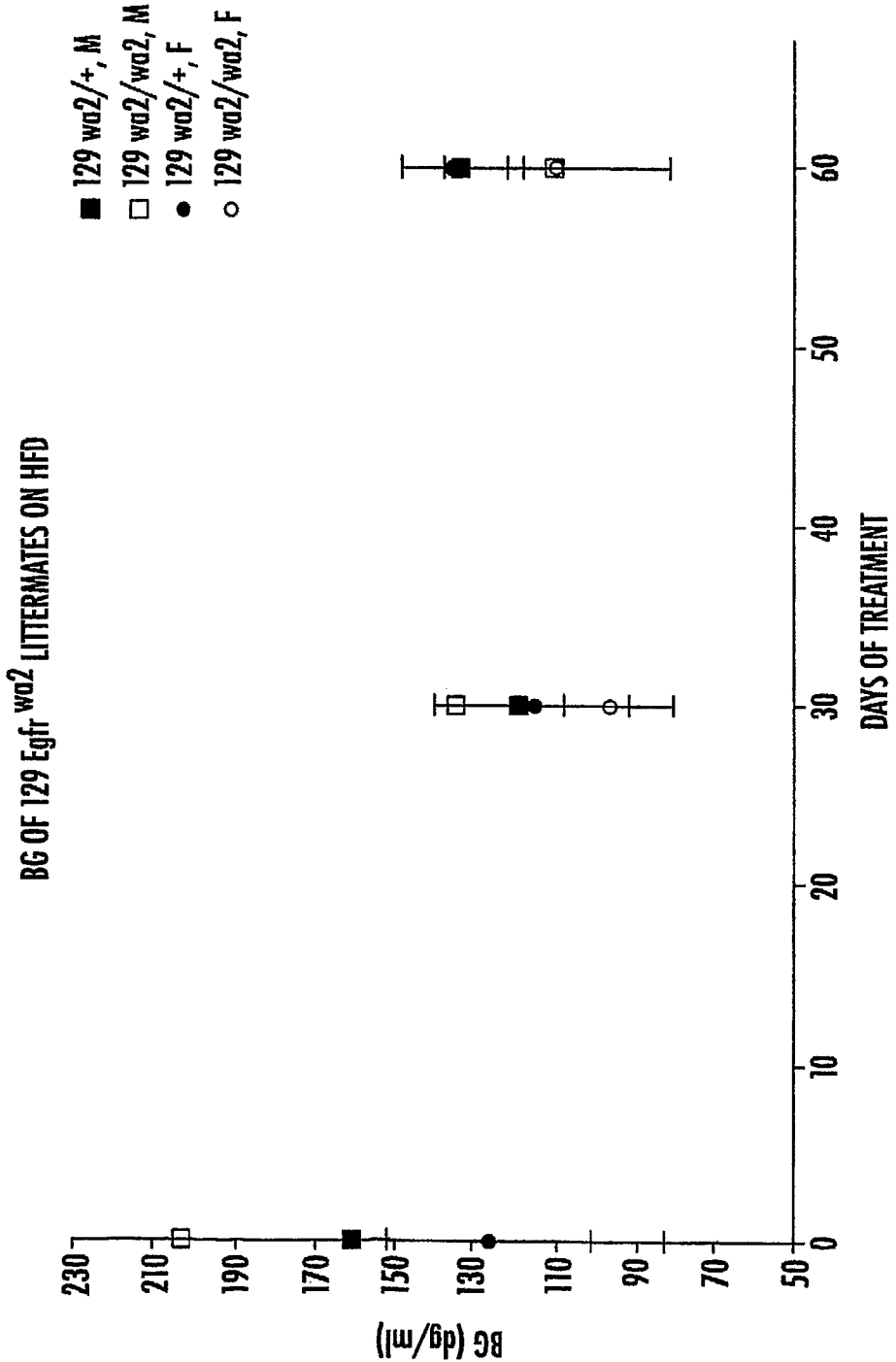
FIG. 6 is a graph depicting blood glucose levels of heterozygous and homozygous wa2 mice on a 129 background fed a high fat diet for up to about 2 months. Solid squares (■) correspond to heterozygous male mice, solid circles (●) correspond to heterozygous female mice, open squares (□) correspond to homozygous male wa2 mice, and open circles (○) correspond to homozygous female wa2 mice.

FIG. 6 depicts blood glucose levels of heterozygous and homozygous wa2 mice on a 129 background fed a high fat diet for up to about 2 months. The data include measurements of 2 heterozygous male mice at days 0, 30, and 60; 1 homozygous male mouse at days 0, 30, and 60; 6 heterozygous female mice at day 0 and 10 heterozygous female mice at days 30 and 60; 4 homozygous female mice at day 0; and 6 homozygous female mice at days 30 and 60. Statistics based on the Wilcoxon rank sum test were calculated as described with respect to the data shown in FIG. 3. The results of the statistical analysis are as follows: baseline: $p<0.99$ females; 30 days: $p<0.10$ females; 60 days: $p<0.03$ females.

Figure 7:
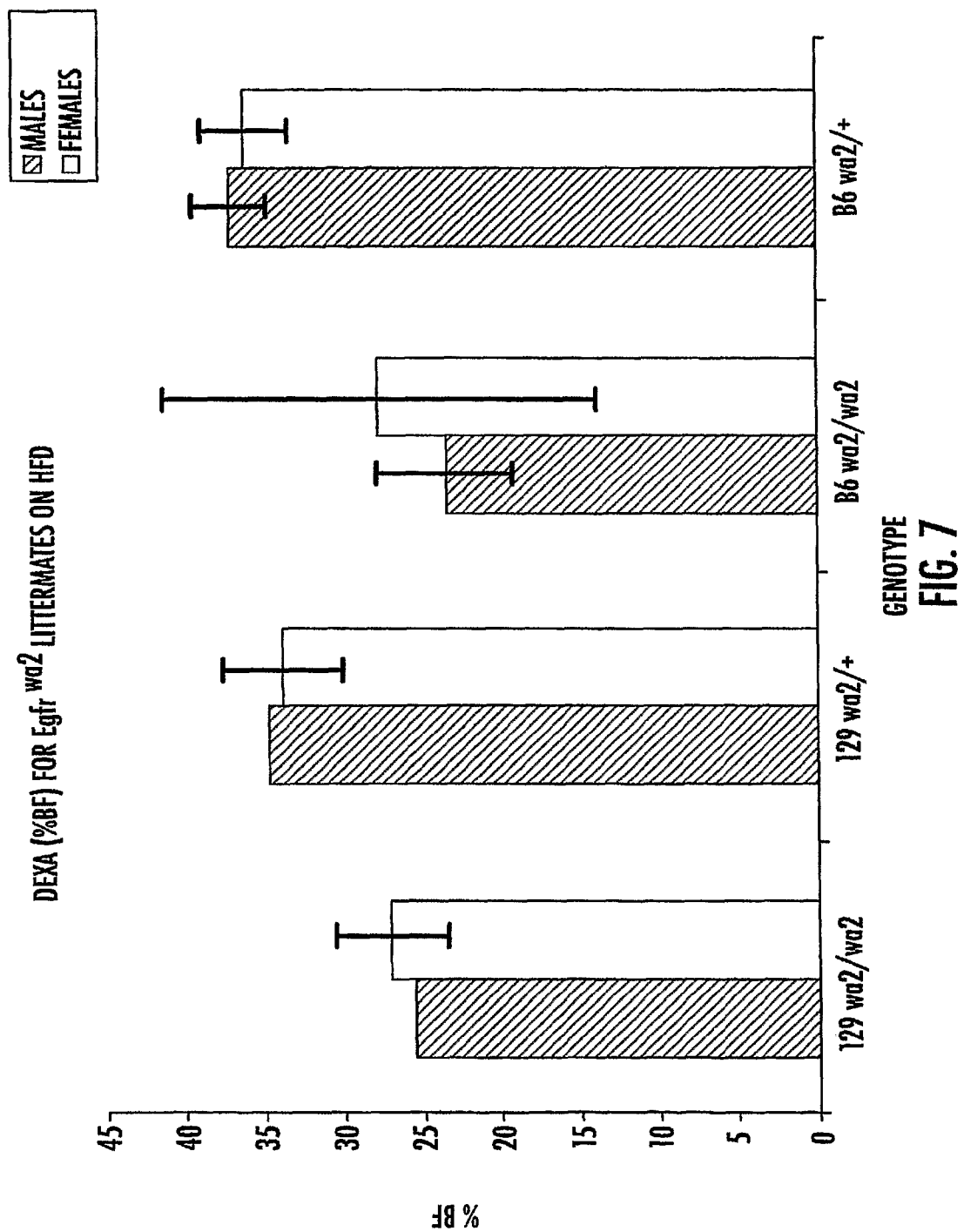
FIG. 7 is a bar graph depicting the results of percent body fat as analyzed by dual-energy x-ray absorptiometry (DEXA) on all littermates after being on the HFD for about 2 months. Dark gray bars correspond to male mice and light gray bars correspond to female mice.

FIG. 7 depicts the results of percent body fat as analyzed by dual-energy x-ray absorptiometry (DEXA) on all littermates after being on the HFD for about 2 months. Data for males (dark gray bars) and females (light gray bars) are presented ±2 standard deviations for $129^{wa2/wa2}$, $129^{wa2/+}$, $C57BL/6^{wa2/wa2}$, and $C57BL/6^{wa2/+}$ mice.

Figure 8:
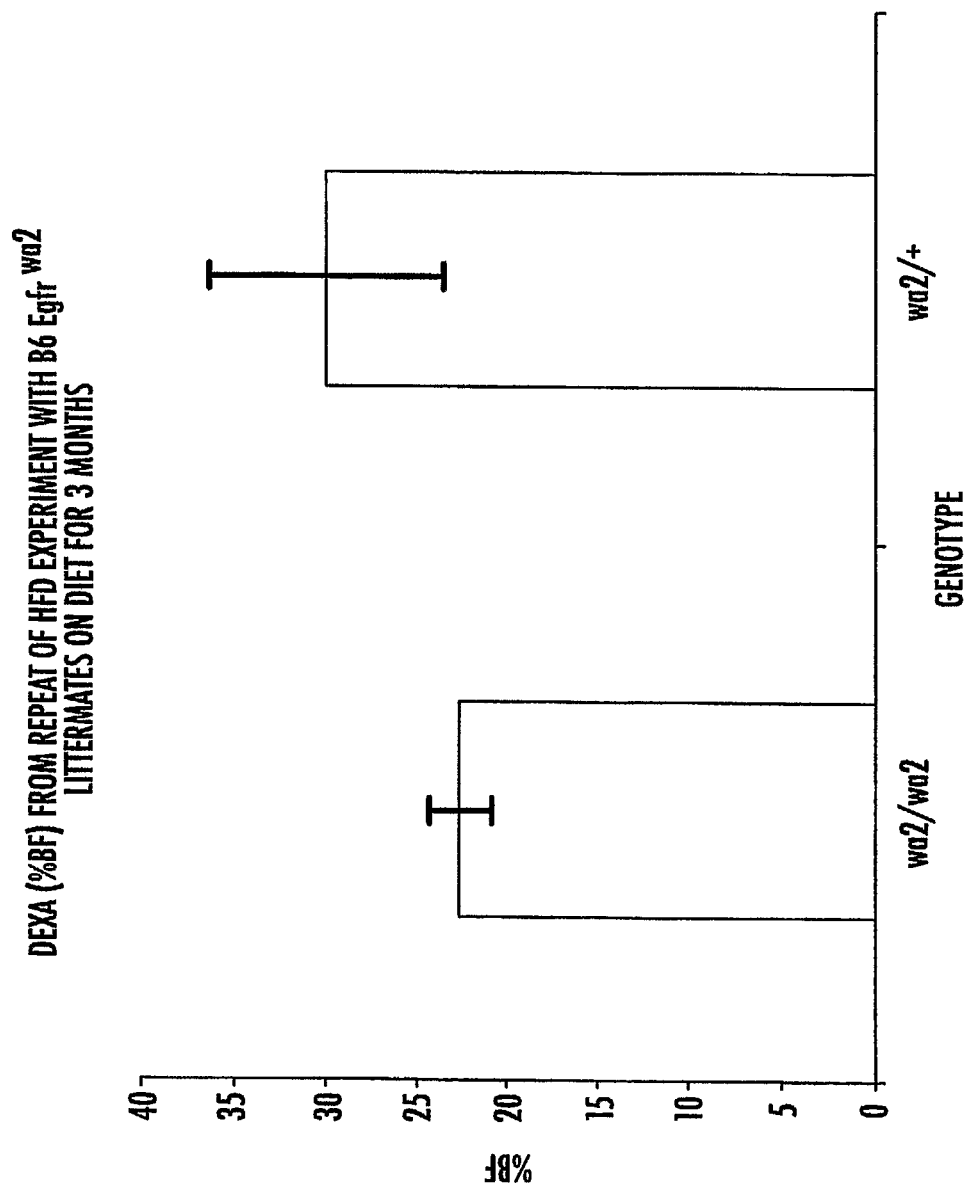
FIG. 8 is a bar graph depicting the results of percent body fat as analyzed by dual-energy x-ray absorptiometry (DEXA) on all littermates after being on the HFD for about 2 months.

FIG. 8 depicts the results of percent body fat as analyzed by dual-energy x-ray absorptiometry (DEXA) on all littermates after being on the HFD for about 2 months. These data are grouped for both strains together distinguished by genotype (i.e., wa2/wa2 or wa2/+), ±2 standard deviations.

Example 2

The results of Example 1 demonstrate EGFR can be a target for drugs that can inhibit the accumulation of adipose tissue, thereby reducing obesity and its associated medical risks. In order to further elaborate on this finding, wild-type mice were treated with an exemplary Egfr-specific inhibitor, AG 1478 (4-(3-Chloroanillino)-6,7-dimethoxyquinazoline, available from A.G. Scientific, Inc., San Diego, Calif., United States of America), and placed on a high fat diet to determine if the inhibitor could effect a reduction in adipose tissue accumulation in the mice. As shown in FIGS. 9-12, the inhibitor successfully inhibited the accumulation of adipose tissue in mice fed a high fat diet, as compared to control mice fed a high fat diet without treatment with the inhibitor.

FIGS. 9-12 depict the results of C57BL/6 male mice exposed either to a high fat diet (HFD; 45% kcal from fat) or the HFD base diet plus the EGFR small molecule inhibitor AG1478 (144 ppm) for about 1 month. The mice were approximately 6 weeks old when started on the dietary study. Male littermates were housed together, so the data are shown as the mean per cage. There is an n of 6 for the mice on the HFD+inhibitor (INH), with two test groups of 6 (HFD+INH1 and HFD+INH2) and an n of 4 for the HFD cage.

Figure 9:
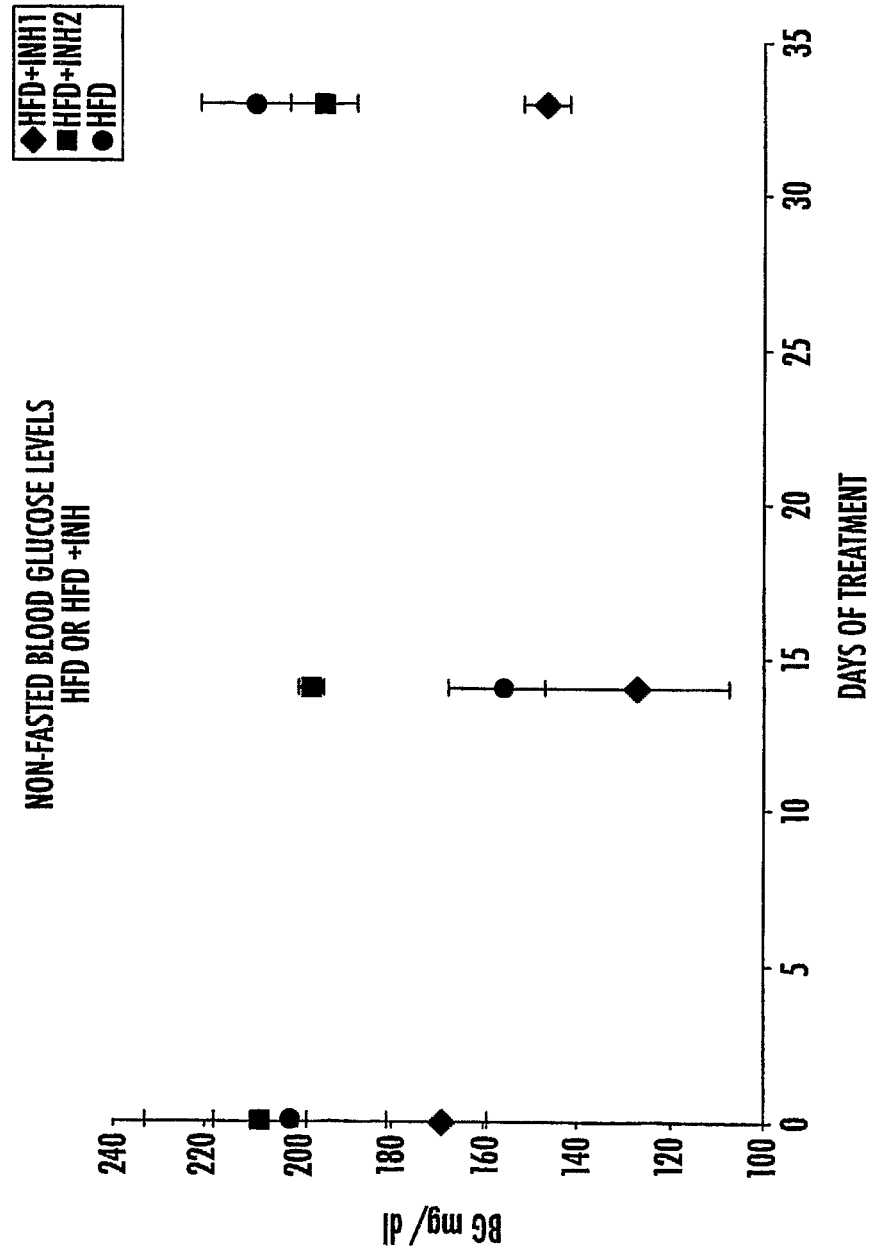
FIG. 9 is a graph depicting the results of non-fasted glucose levels from C57BL/6 male mice exposed either to a high fat diet (HFD; 45% kcal from fat; represented by solid circles (●)) or the HFD base diet plus the EGFR small molecule inhibitor AG1478 (144 ppm; represented by solid diamonds (♦) for population HFD+INH1 or solid squares (■) for population HFD+INH2) for about 1 month.
Figure 10:
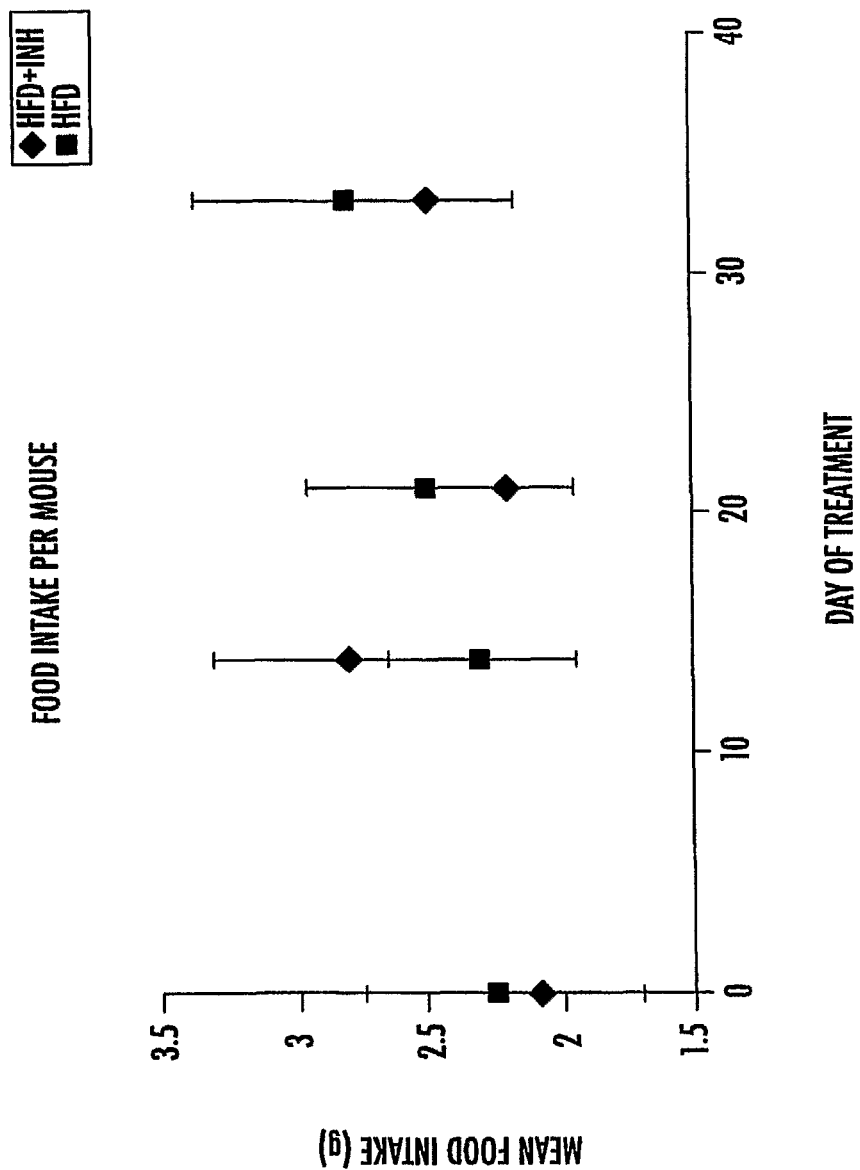
FIG. 10 is a graph, depicting the results of food consumption per mouse per day (estimated from food total food remaining per day) from C57BL/6 male mice exposed either to a high fat diet (HFD; 45% kcal from fat; represented by solid circles (■)) or the HFD base diet plus the EGFR small molecule inhibitor AG1478 (144 ppm; represented by solid diamonds (♦)) for about 1 month.

FIG. 9 depicts the results of non-fasted glucose levels. FIG. 10 depicts the results of food consumption per mouse per day (estimated from total food remaining per day) and demonstrates no significant difference between HFD+INH mice as compared to control mice (HFD), suggesting the inhibitor does not affect food intake.

Figure 11:
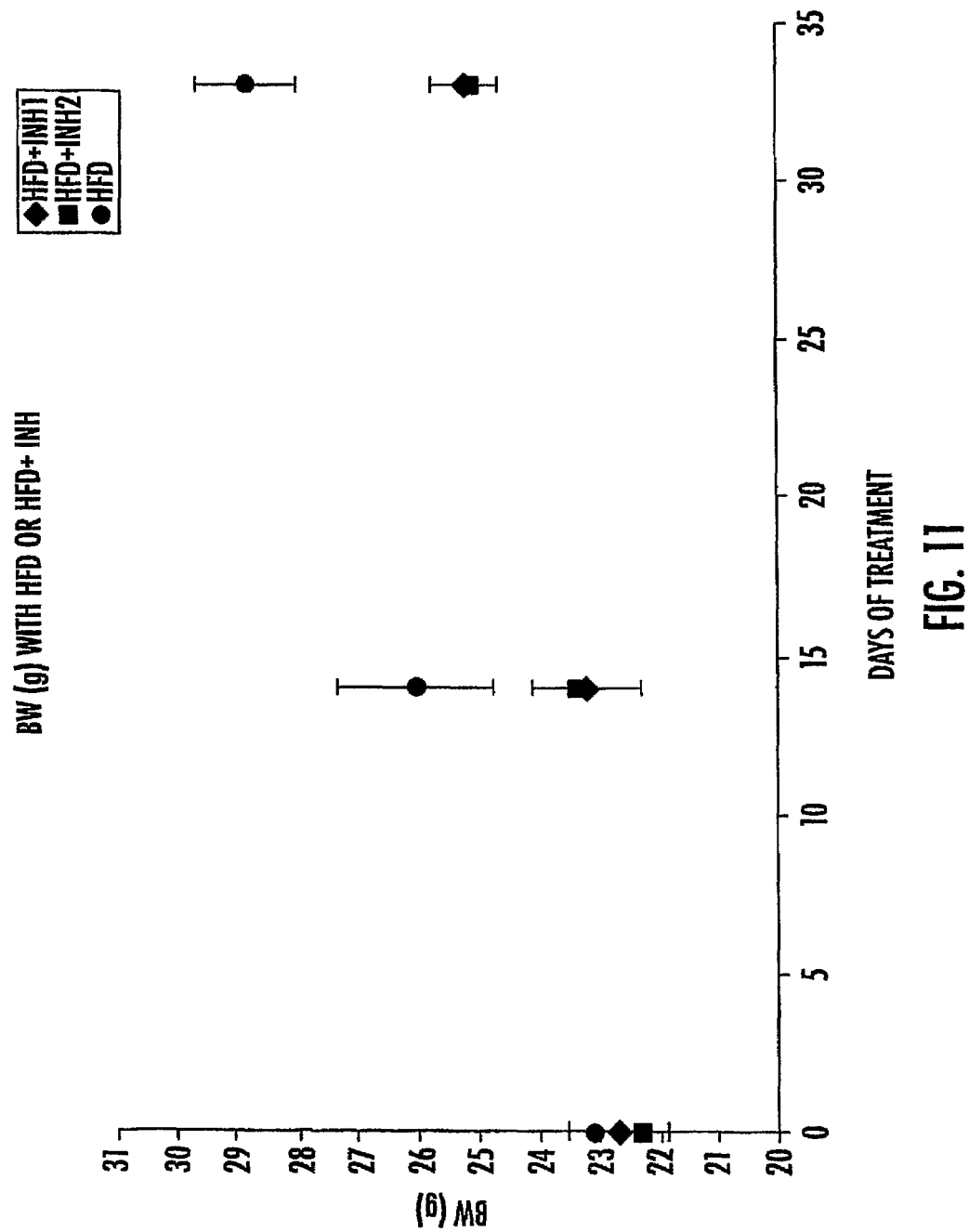
FIG. 11 is a graph depicting the results of body weight per mouse from C57BL/6 male mice exposed either to a high fat diet (HFD; 45% kcal from fat; represented by solid circles (●)) or the HFD base diet plus the EGFR small molecule inhibitor AG1478 (144 ppm; represented by solid diamonds (♦) for population HFD+INH1 or solid squares (■) for population HFD+INH2) for about 1 month.
Figure 12:
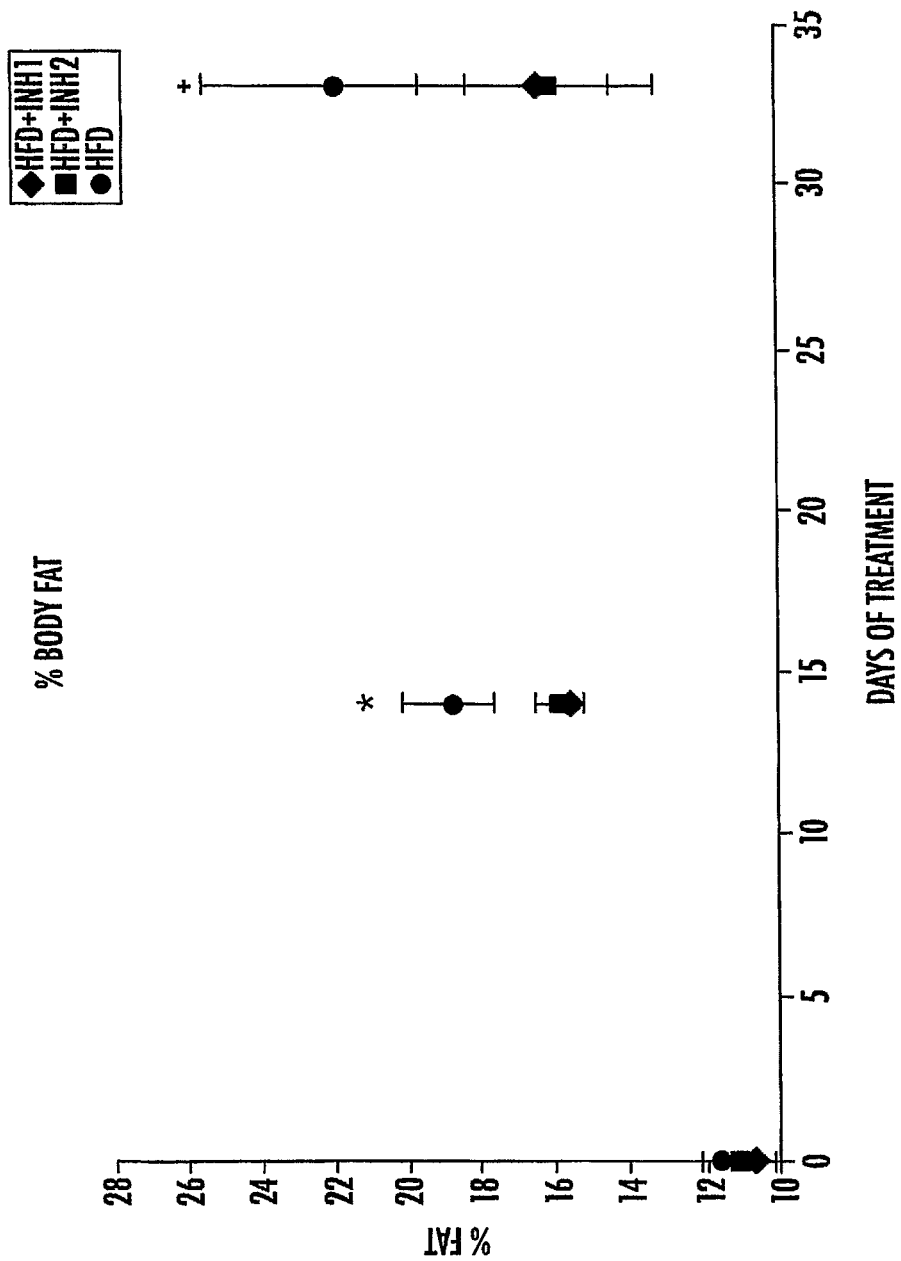
FIG. 12 is a graph depicting the results of percent body fat from C57BL/6 male mice exposed either to a high fat diet (HFD; 45% kcal from fat; represented by solid circles (●)) or the HFD base diet plus the EGFR small molecule inhibitor AG1478 (144 ppm; represented by solid diamonds (♦) for population HFD+INH1 or solid squares (■) for population HFD+INH2) for about 1 month as analyzed by dual-energy x-ray absorptiometry (DEXA).

FIG. 11 depicts the results of body weight per mouse and FIG. 12 depicts the results of percent body fat as analyzed by dual-energy x-ray absorptiometry (DEXA). As can be seen in FIGS. 11 and 12, mice administered the inhibitor gained less body weight over a one month time period than did control mice. Further, the reduction in weight gain was due to a reduction in adipose tissue accumulation, as compared to control mice.

Example 3

In order to determine if the short-term effects on weight gain due to the inhibitor action were applicable over a longer time period, the experiments of Example 2 were extended over six months.

Baseline measurements (body weights, blood glucose, and percent body fat) were taken of 2-month-old male C57 BL/6J (B6) mice which were then housed individually and randomly assigned to receive either HFD or HFD+Inhibitor A (AG 1478). Measurements were again assessed at 1, 2 and 6 months of treatment. All mice were sacrificed at month 6. At sacrifice, blood was collected for clinical chemistry. Heart, liver and fat depots were also dissected and weighed. Results are expressed as mean+/−STD and are shown in FIGS. 13-17. A two-sided unpaired student's t-test was used for preliminary statistical analysis.

Figure 13:
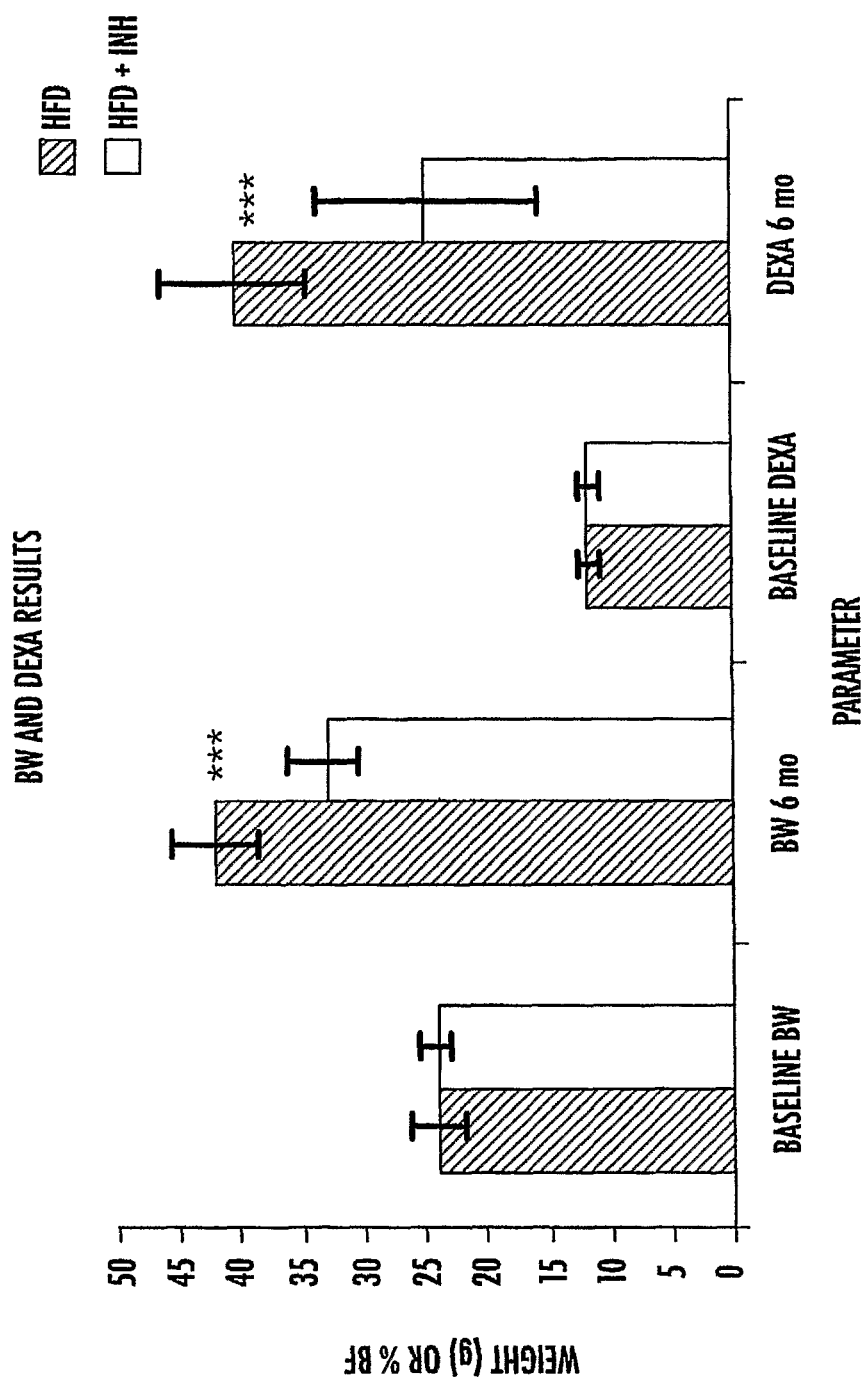
FIG. 13 is a bar graph depicting body weight (BW) and percent body fat as assessed by DEXA after a six month treatment period. Light gray bars correspond to mice exposed to an HFD (HFD) and dark gray bars correspond to mice exposed to the HFD base diet plus the EGFR small molecule inhibitor AG1478 (HFD+INH). Unpaired t-test: Baseline BW, ns; BW 6 mos, $p<9.75E1X-05$ vs. HFD; Baseline DEXA, ns; DEXA 6 mos, $p<0.001$ vs. HFD.
Figure 14:
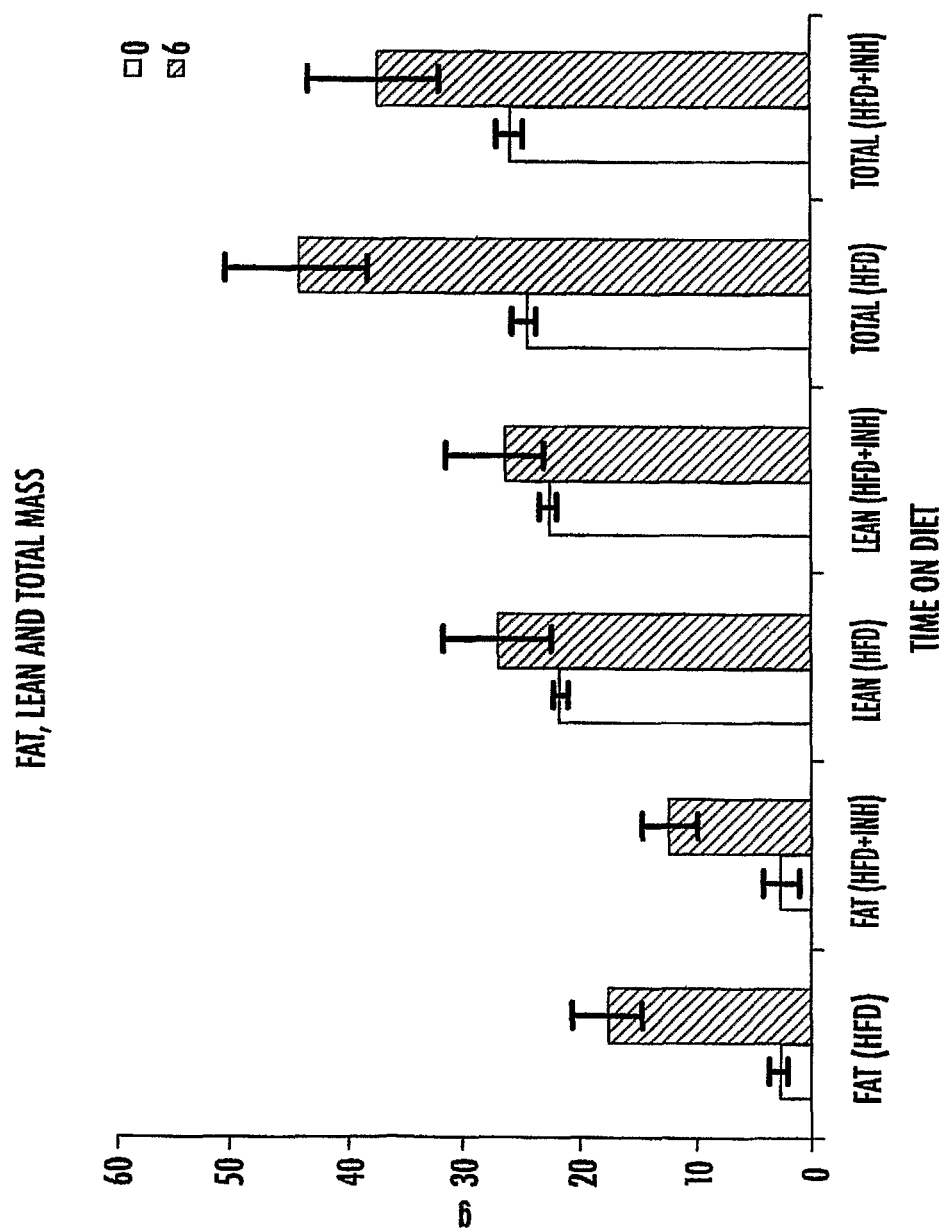
FIG. 14 is a bar graph depicting B6 mice fed an HFD supplemented with inhibitor A AG1478 (HFD+INH), showing no change in lean body mass by six months as compared to mice on HFD alone (HFD). Light gray bars correspond to mass at baseline and dark gray bars correspond to mass after six months of treatment on HFD or HFD+INH. n=8 mice per group; $p<0.03$ vs. HFD.

As shown in FIG. 13, body weight (BW) and percent body fat as assessed by DEXA are significantly decreased in B6 male mice maintained on a HFD with inhibitor A (AG 1478) as compared to HFD alone for 6 months (n=8 mice per group. FIG. 14 shows that B6 mice fed the HFD supplemented with inhibitor A have no change in lean body mass, but decreased fat mass at six months on the diet as compared to mice on HFD alone (n=8 mice per group).

Figure 15:
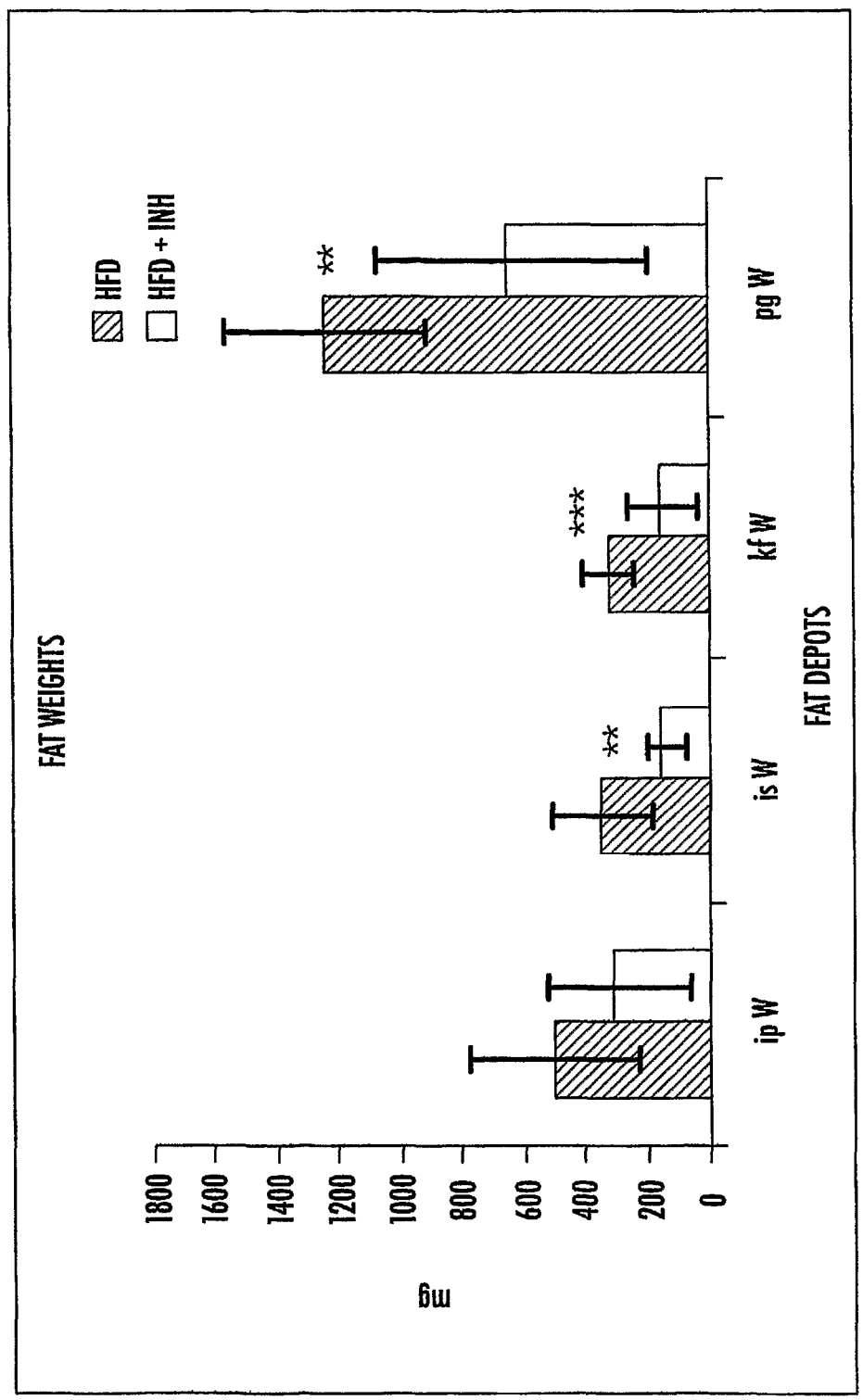
FIG. 15 is a graph depicting changes in fat mass in all four major fat depots in mice fed HFD or HFD+Inhibitor A. ip W=intraperitoneal fat weight; is W=intrascapular fat weight; kf W=kidney fat weight; pg W=perigonadal fat weight. Unpaired t-test: ip W, ns; is W, $p<0.009$ vs. HFD; kf W, $p<0.004$ vs. HFD; pg W: $p<0.008$ vs. HFD.
Figure 16:
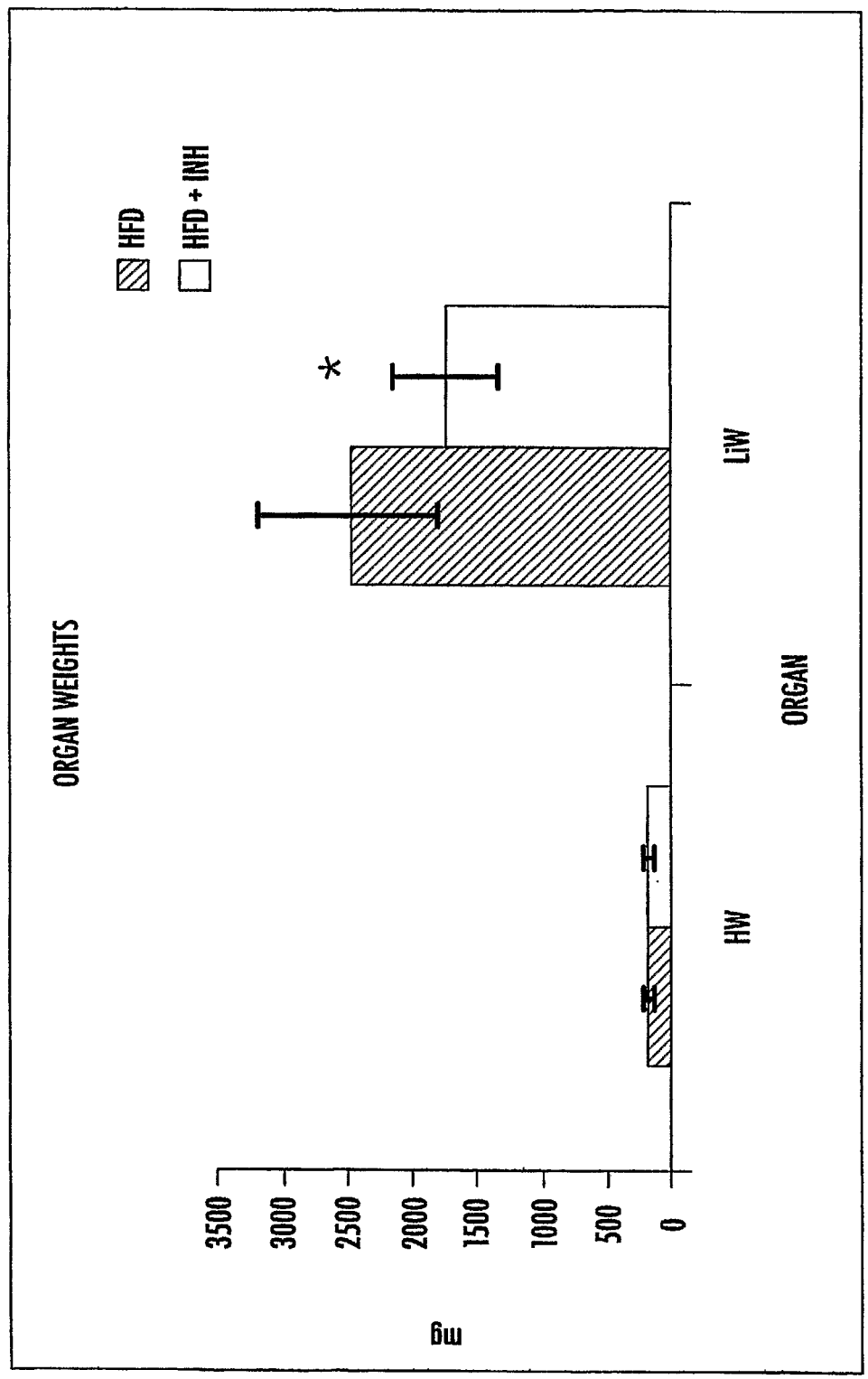
FIG. 16 is a bar graph depicting changes in organ weights in mice fed HFD or HFD+Inhibitor A. Light gray bars correspond to mice exposed to an HFD (HFD) and dark gray bars correspond to mice exposed to the HFD base diet plus the EGFR small molecule inhibitor AG1478 (HFD+INH). Unpaired t-test: HW, ns; LiW: $p<0.02$ vs. HFD.

Dissection of B6 mice after 6 months on the respective diets reveals decreased fat mass in all four major fat depots in mice fed HFD+Inhibitor A (FIG. 15). As shown in FIG. 16, no significant differences are detected in gross heart weights. However, gross liver weight is significantly reduced in B6 mice on HFD+Inhibitor A (AG 1478) as compared to HFD.

Figure 17:
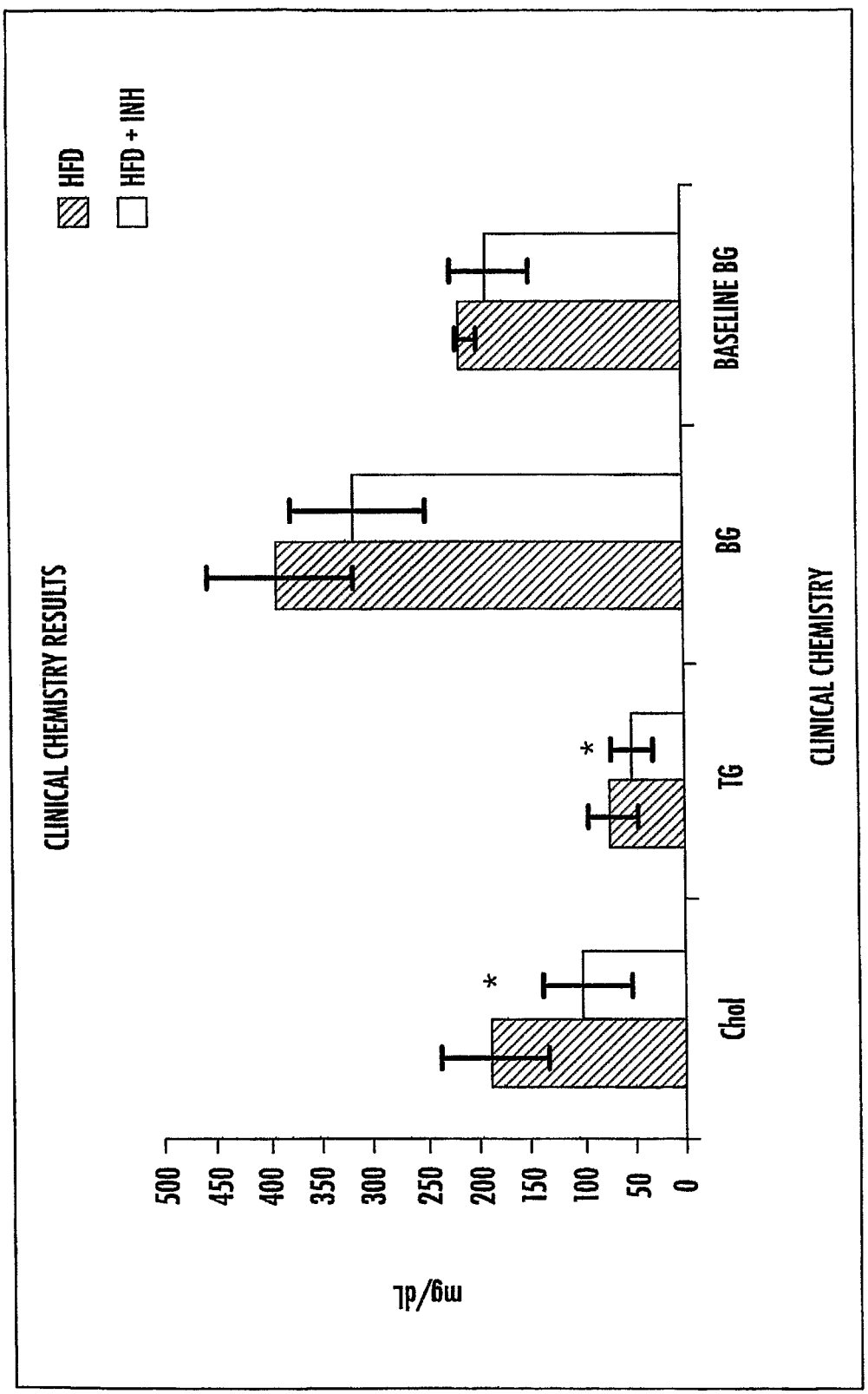
FIG. 17 is a bar graph depicting clinical chemistry results in mice fed HFD or HFD+Inhibitor A. Light gray bars correspond to mice exposed to an HFD (HFD) and dark gray bars correspond to mice exposed to the HFD base diet plus the EGFR small molecule inhibitor AG1478 (HFD+INH). Chol=total cholesterol; TG=total triglycerides; BG=blood glucose. Unpaired t-test: Chol, $p<0.053$ vs. HFD n=8 HFD, 7 HFD+INH; TG, $p<0.038$ vs. HFD n=8; BG: $p<0.07$ vs. HFD, n=8 HFD, 6 HFD+INH; Baseline BG, ns.

Clinical chemistry results are shown in FIG. 17. Plasma was harvested from 7-8 mice per group after 6 months on the respective diets. Total cholesterol and triglyceride levels were significantly lower in B6 mice receiving HFD+Inhibitor A. For comparison, baseline blood glucose measurements are also shown.

Example 4

In order to assess whether EGFR inhibitors can effect weight loss or stasis in an already obese subject, obese mice were administered an EGFR inhibitor and body mass and chemistry measurements made over time while maintaining a HFD. Specifically, baseline measurements were taken of 2 month-old male B6 mice, which were then housed individually and placed on a HFD for 2 months. Body weights, blood glucose, and percent body fat were assessed at this time point, and mice were randomly assigned to two groups. Group 1 (Grp1) was continuously fed the HFD, while Group 2 (Grp2) was switched to the HFD+INH after the initial two months. Measurements were again assessed at 1 and 3 months after the diet switch (experimental month 3 and 5). All mice were sacrificed at month 5. At sacrifice, blood was collected for clinical chemistry and heart, liver and fat depots were dissected and weighed. Results are expressed as mean+/−STD and are shown in FIGS. 18-21. A two-sided unpaired student's t-test was used for preliminary statistical analysis.

Figure 18:
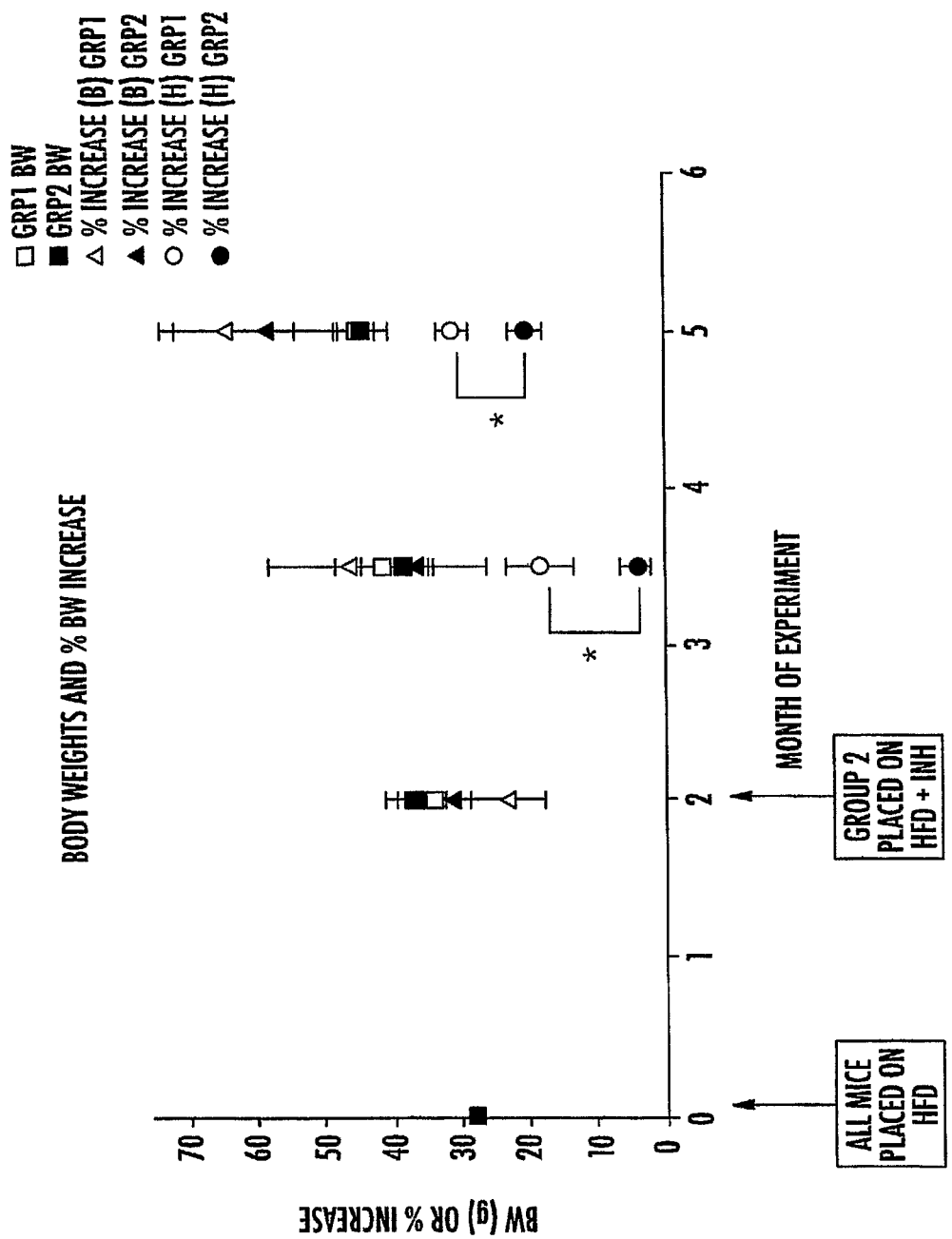
FIG. 18 is a graph depicting body weights and percent body weight increase in Group 1 (HFD only) and Group 2 (HDF initially and then HFD+Inhibitor A after two months). Open squares (□) represent Group 1 body weight, solid squares (■) represent Group 2 body weight, open triangles (Δ) represent the percent increase in body weight compared to baseline body weight of Group 1 mice, closed triangles (▲) represent the percent increase in body weight compared to baseline body weight of Group 2 mice, open circles (○) represent the percent increase in body weight compared to body weight at the time of diet change (i.e., month 2) of Group 1 mice, and closed circles (●) represent the percent increase in body weight compared to body weight at the time of diet change (i.e., month 2) of Group 2 mice. n=4 mice per group; $p<0.02$ vs. Group 1.

FIG. 18 shows body weights and percent body weight increase in Group 1 and Group 2. "% Increase (B)" refers to BW compared to baseline measurements (i.e. month 0). "% Increase (H)" refers to BW compared to BW at the time of diet change (i.e. month 2). As can be seen from FIG. 18, percent increase in BW relative to BW at 2 months on HFD was significantly lower in Group 2 compared to Group 1 after 1 and 3 months on the HFD+Inhibitor A (n=4 mice per group, p<0.02 vs. Group 1).

Figure 19:
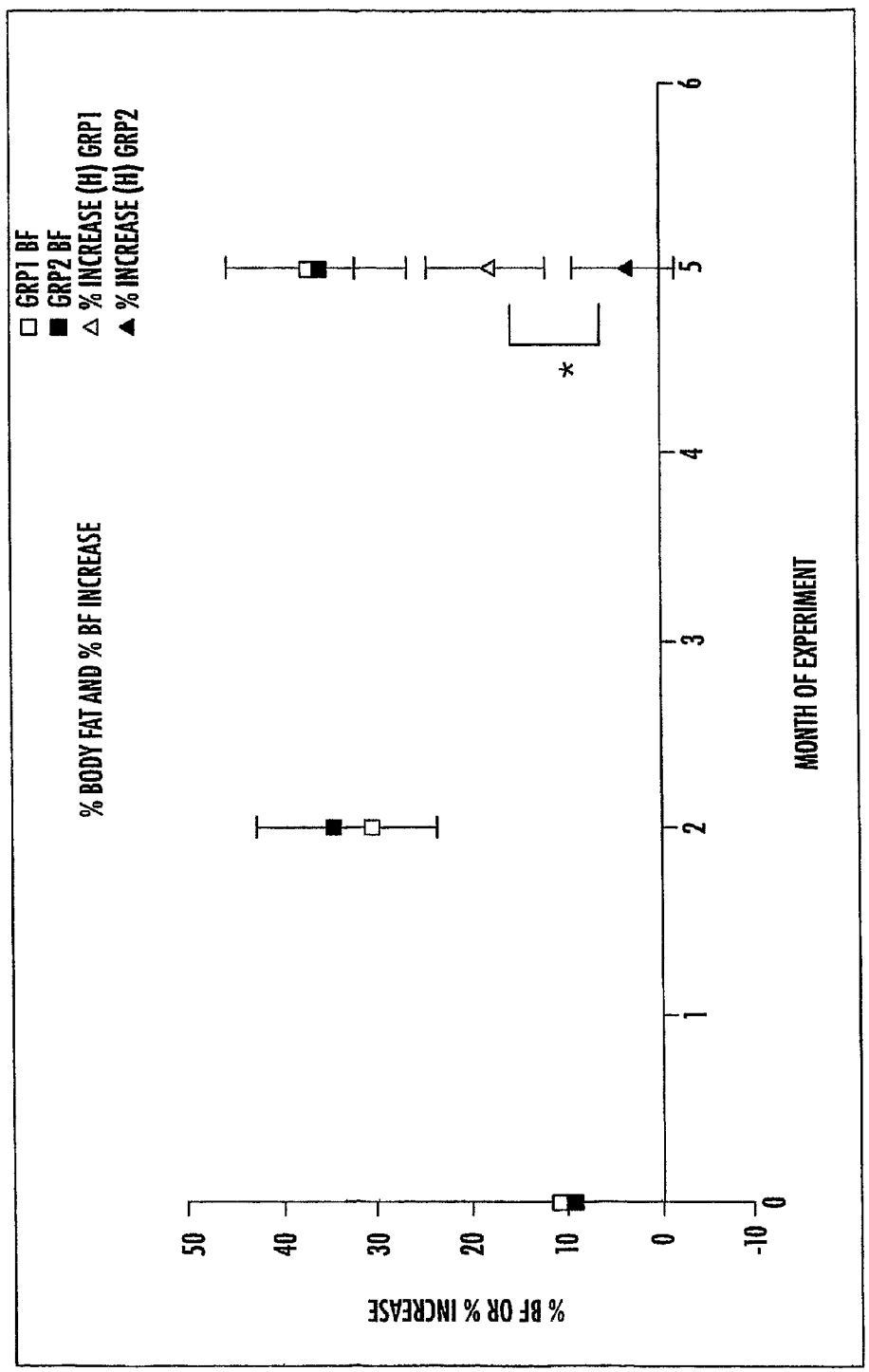
FIG. 19 is a graph depicting percent body fat (% BF) as assessed by DEXA and % BF increase in Group 1 (HFD only) and Group 2 (HDF initially and then HFD+Inhibitor A after two months). Open squares (□) represent Group 1 body weight, solid squares (■) represent Group 2 body weight, open triangles (Δ) represent the percent increase in body fat compared to body fat at the time of diet change (i.e., month 2) of Group 1 mice, and closed triangles (▲) represent the percent increase in body fat compared to body fat at the time of diet change (i.e., month 2) of Group 2 mice. n=4 mice per group; $p<0.02$ vs. Group 1.
Figure 20A:
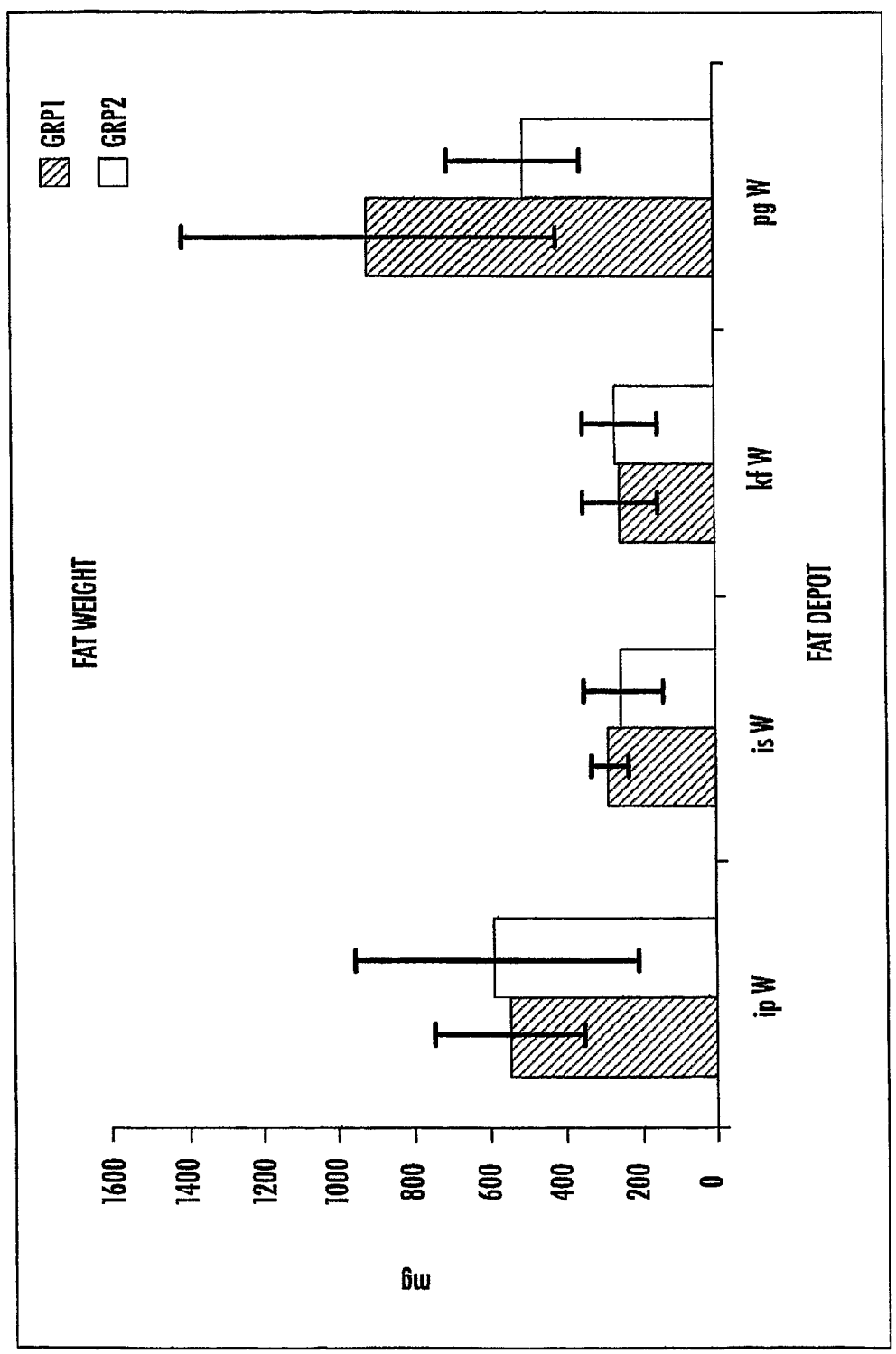
FIGS. 20A and 20B are bar graphs depicting fat depot weights in heart and liver between Group 1 (HFD only) and Group 2 (HDF initially and then HFD+Inhibitor A after two months). Black bars correspond to Group 1 mice and gray bars correspond to Group 2 mice.
Figure 20B:
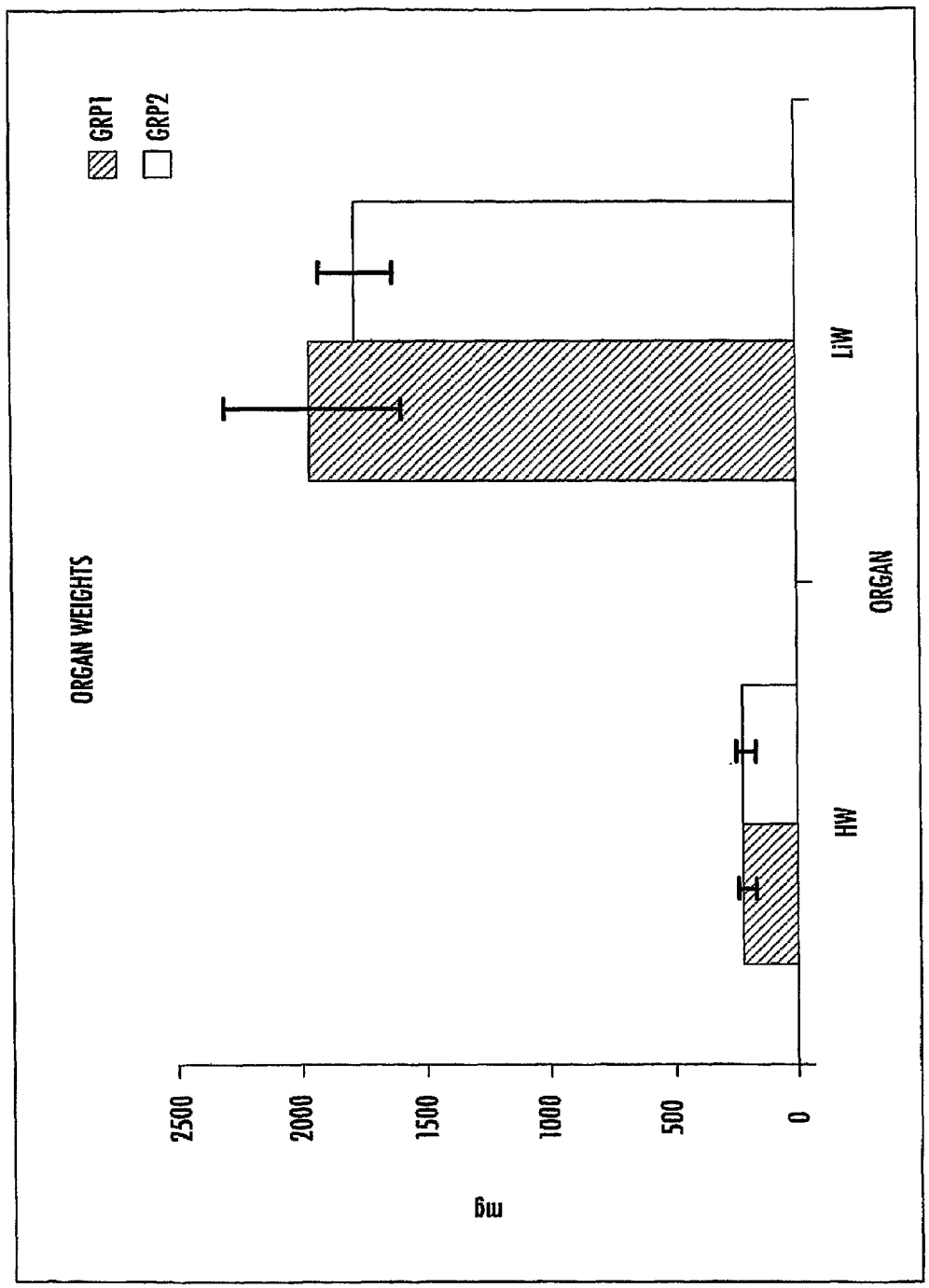

FIG. 19 shows percent body fat (% BF) as assessed by DEXA and % BF increase in Group 1 and 2. "% increase (H)" refers to BF compared to BF at the time of diet change (i.e. month 2). Percent increase in BF (H) was significantly lower in Group 2 compared to Group 1 after 3 months on the HFD+Inhibitor A (n=4 mice per group, p<0.02 vs. Group 1).

Figure 21:
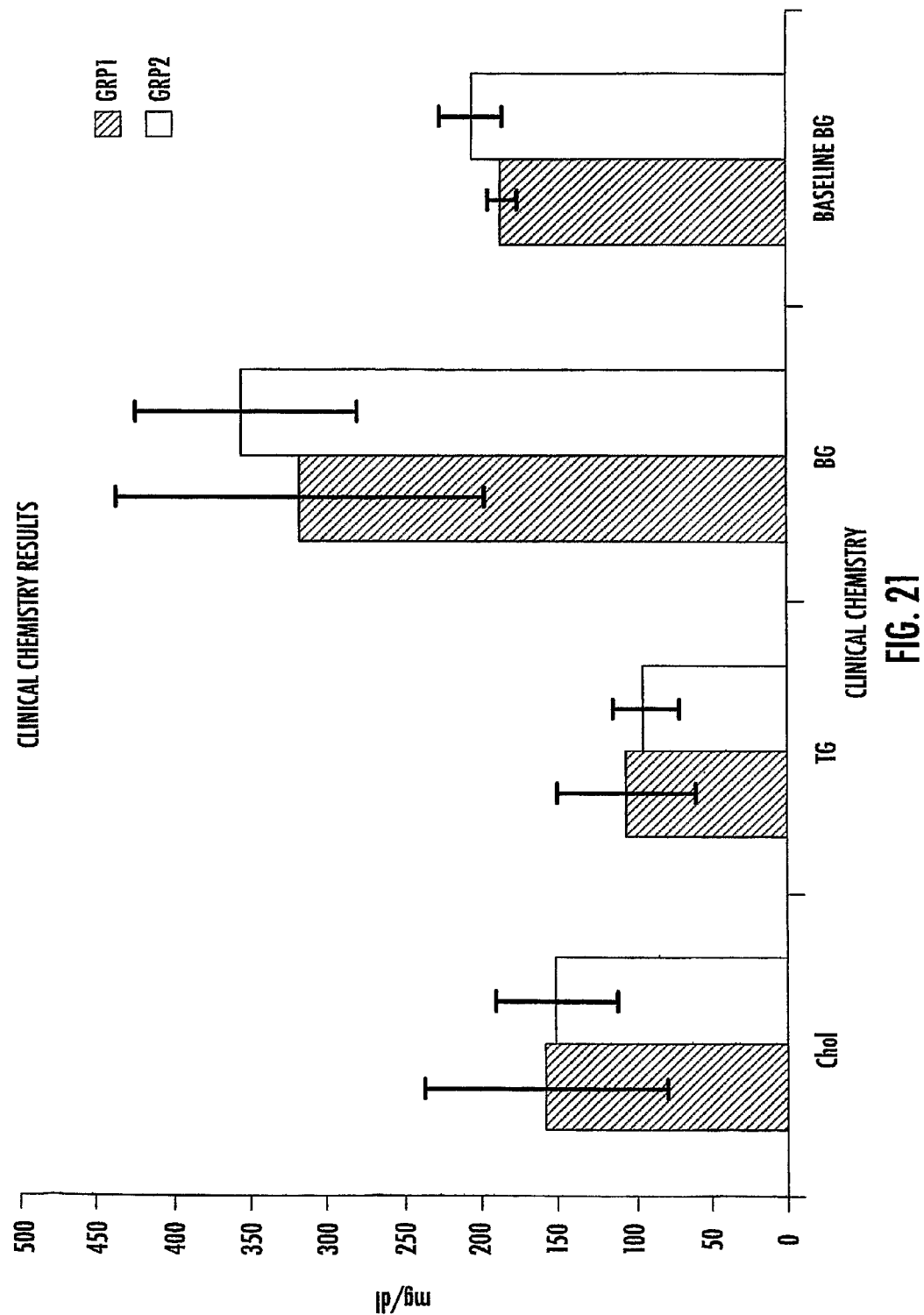
FIG. 21 is a bar graph depicting clinical chemistry results in Group 1 (HFD only) and Group 2 (HDF initially and then HFD+Inhibitor A after two months). Light gray bars correspond to Group 1 mice and dark gray bars correspond to Group 2 mice.

No significant differences were detected in fat depot weights (FIG. 20A) or heart and liver weights (FIG. 20B) between treatment groups (n=4 mice per group). Further, as shown in FIG. 21, no significant differences were detected in total cholesterol, triglyceride or blood glucose levels between treatment groups (n=4 mice per group).

Example 5

In order to assess whether inhibition of EGFR activity only in particular organs and/or systems affected overall subject body weight and/or adipose tissue accumulation, mice having reduced EGFR activity in the small intestine, colon and kidney were generated. Specifically, a Villin Cre line (B6.D2-Tg(Vil-Cre)20Syr from Mouse Repository, Mouse Models of Human Cancers Consortium, National Cancer Institute, U.S. National Institutes of Health, Frederick, Md., U.S.A.) was crossed to Egfr$^{flox}$ mice. When crossed with a strain containing loxP site flanked sequence of interest, Cre-mediated recombination results in tissue-specific deletion of the target. el Marjou et al. (2004) Genesis 39(3):186-93. The Villin Cre line has homogenous Cre recombinase expression in the small intestine, colon and proximal tubule of the kidney.

Figure 22:
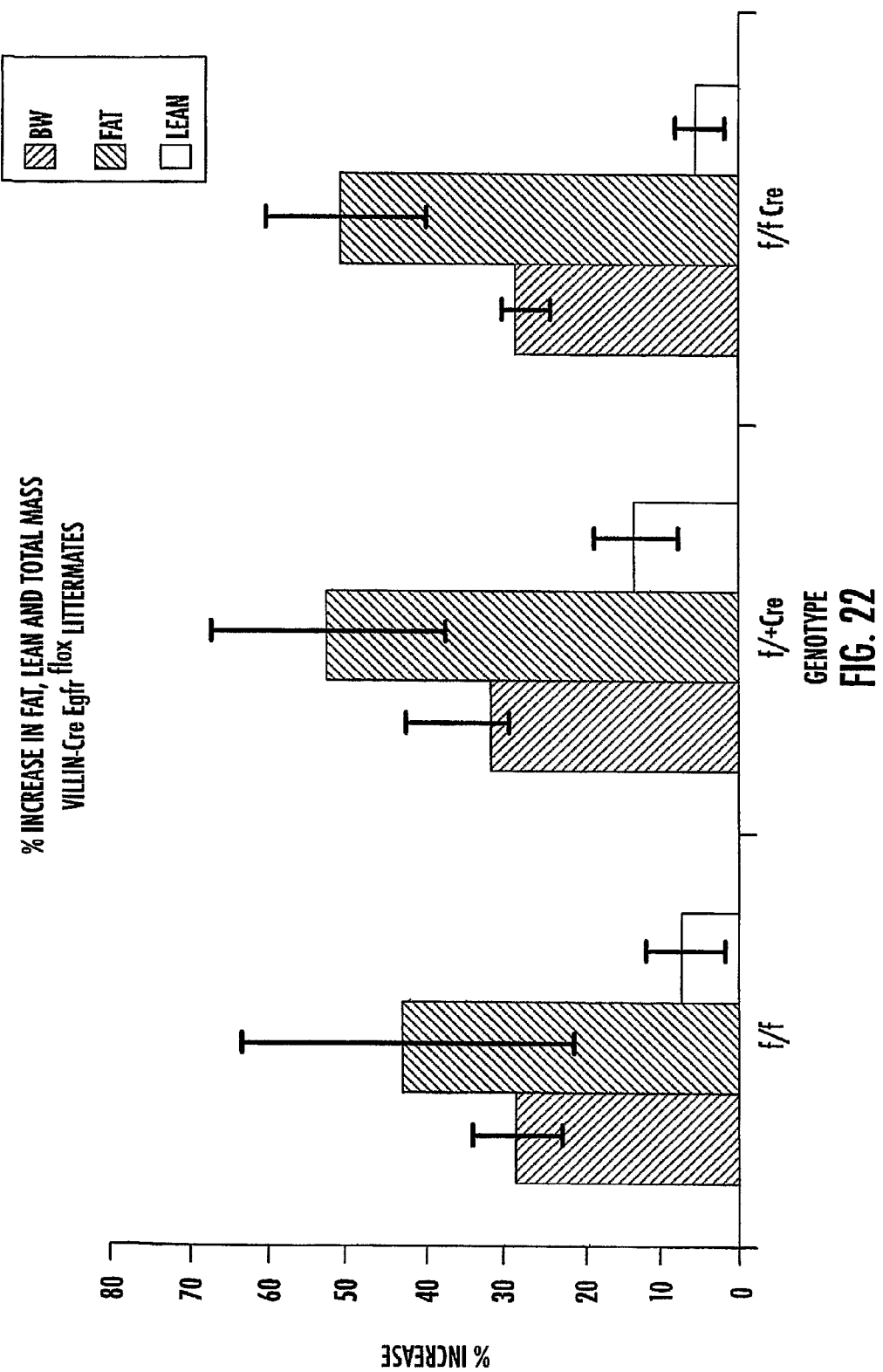
FIG. 22 is a bar graph depicting the percent increase in total, lean, and fat mass of $Egfr^{flox/flox} \times Egfr^{flox/+}$Villin $Cre^{Tg/+}$ cross littermates, as measured by a change from baseline MRI. Light gray bars correspond to lean mass, medium gray bars correspond to fat mass, and black bars correspond to total mass (BW). n=2 f/f (M), 3 f/+Cre (F) and 3 f/f Cre mice (1M, 2F).

Baseline MRI were taken of 2 month-old littermates from a Egfr$^{flox/flox}$× Egfr$^{flox/+}$Villin Cre$^{Tg/+}$ cross. These mice were then placed on a HFD for three months, at the end of this time, MRIs were again taken. Results are presented in FIG. 22 as percent increase relative to baseline measurements.

Example 6

In order to further assess whether inhibition of EGFR activity only in particular organs and/or systems affected overall subject body weight and/or adipose tissue accumulation, mice having reduced EGFR activity in the central nervous system (CNS) were generated. Specifically, a GFAP Cre line (FVB-Tg(GFAP-cre)25Mes/J from JAX® Mice, The Jackson Laboratory, Bar Harbor, Me., U.S.A.) was crossed to Egfr$^{flox}$ mice for use in this experiment. The GFAP Cre transgenic mouse strain expresses Cre recombinase under the control of the human glial fibrillary acidic protein promoter (GFAP). Zhuo et al. (2001) Genesis 31(2):85-94. When crossed with a strain containing loxP site flanked sequence of interest, Cre-mediated recombination results in tissue-specific deletion of the target. Recombination occurs primarily in the central nervous system, affecting astrocytes, oligodendroglia, ependyma and some neurons. Expression activity is also present in periportal cells of the liver.

Figure 23:
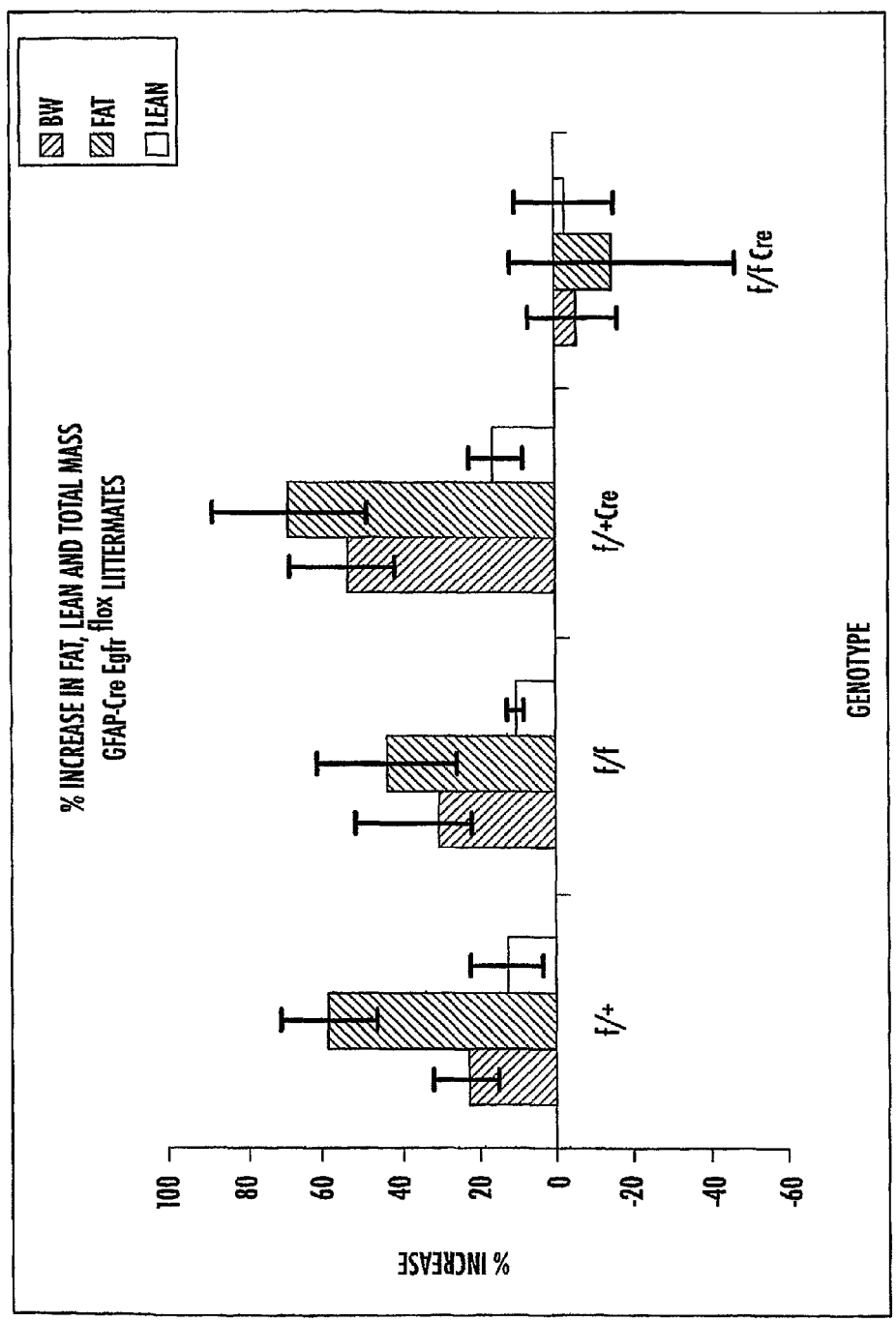
FIG. 23 is a bar graph depicting the percent increase in total, lean, and fat mass of $Egfr^{flox/flox} \times Egfr^{flox/+}$GFAP $Cre^{Tg/+}$ cross littermates, as measured by a change from baseline MRI. Light gray bars correspond to lean mass, medium gray bars correspond to fat mass, and black bars correspond to total mass (BW). n=2 f/f (M), 3 f/+Cre (F) and 3 f/f Cre mice (1M, 2F). n=3 f/+(2M, 1F), 3 f/f (3F), 2 f/+Cre (M) and 4 f/f Cre (2M, 2F).

Baseline MRI were taken of 2 month-old littermates from a Egfr$^{flox/flox}$×Egfr$^{flox/+}$GFAP Cre$^{Tg/+}$ cross. These mice were then placed on a HFD for three months, at the end of this time, MRIs were again taken. Results are presented in FIG. 23 as percent increase relative to baseline measurements. FIG. 23 demonstrates that mice with reduced EGFR activity in the CNS did not have a significant increase in lean mass, fat mass or total mass when maintained on an HFD for three months. In direct contrast, control mice (f/+, f/f, and f/+ Cre) showed significant gains in total mass and fat mass under the same conditions.

REFERENCES

The references listed below, as well as all references cited in the specification, are incorporated herein by reference to the extent that they supplement, explain, provide a background for, or teach methodology, techniques, and/or compositions employed herein.

Bass (2001) Nature 411:428-429.
Bernstein et al. (2001) Nature 409:363-366.
Bray et al. (1999) Obes. Res. 189-98.
Brommage (2003) J Physiol Endocrinol Metab 285: E454-459.
Canadian Patent Application No. 2,359,180.
Davidson et al. (1999) JAMA 281:23542.
Douglas et al. (1983) Int. J. Obes. 7:591-5.
el Marjou et al. (2004) Genesis 39(3): 186-93.
Elbashir et al. (2001a) Nature 411:494-498.
Elbashir et al. (2001b) Genes Dev 15:188-200.
Fire (1999) Trends Genet 15:358-363.
Fire et al. (1998) Nature 391:806-811.
Goldstein et al. (1995) Clin Cancer Res. 1:1311-1318.
Guy Grand et al. (1989) Lancet 2:1142-5.
Hammond et al. (2000) Nature 404:293-296.
Herbst et al. (2004) Nat Rev Cancer 4:956-65.
Luetteke et al. (1994) Genes Dev 8:399-413.
National Institutes of Health, Clinical Guidelines on the Identification, Evaluation, and Treatment of Overweight and Obesity in Adults (1998).
Nykanen et al. (2001) Cell 107:309-321.
PCT International Publication No. WO 00/01846.
PCT International Publication No. WO 00/44895.
PCT International Publication No. WO 00/44914.
PCT International Publication No. WO 00/63364.
PCT International Publication No. WO 01/04313.
PCT International Publication No. WO 01/29058.
PCT International Publication No. WO 01/36646.
PCT International Publication No. WO 01/36646.
PCT International Publication No. WO 01/68836.
PCT International Publication No. WO 01/75164.
PCT International Publication No. WO 01/92513.
PCT International Publication No. WO 02/055692.
PCT International Publication No. WO 02/055693.
PCT International Publication No. WO 02/44321.
PCT International Publication No. WO 93/25521.
PCT International Publication No. WO 99/07409.
PCT International Publication No. WO 99/32619
PCT International Publication No. WO 99/32619.
PCT Patent Application No. PCT/US02/22010.
U.S. Pat. No. 4,196,265.
U.S. Pat. No. 5,234,933.
U.S. Pat. No. 5,326,902.
U.S. Pat. No. 5,352,660.
U.S. Pat. No. 5,422,245.
U.S. Pat. No. 5,627,158.
U.S. Pat. No. 5,645,999.
U.S. Pat. No. 5,734,033.
U.S. Pat. No. 5,739,278.
U.S. Pat. No. 5,786,152.
U.S. Pat. No. 5,837,479.
Wianny & Zernicka-Goetz (1999) Nature Cell Biol 2:70-75.
Yarden (2001) Eur J Cancer 37 (Suppl 4):3-8.
Zhuo et al. (2001) Genesis 31(2):85-94.

It will be understood that various details of the presently disclosed subject matter may be changed without departing from the scope of the present subject matter. Furthermore, the foregoing description is for the purpose of illustration only, and not for the purpose of limitation.

What is claimed is:

1. A method of treating obesity in a subject, the method comprising administering to the subject an effective amount of a compound, wherein the effective amount is effective in reducing an activity of an epidermal growth factor receptor (EGFR) in the subject, whereby obesity in the subject is treated.

2. The method of claim 1, wherein the step of administering comprises administering an effective amount of a composition that modulates expression of the EGFR in the subject.

3. The method of claim 2, wherein the composition that modulates expression of the EGFR comprises an antisense oligonucleotide.

4. The method of claim 1, wherein the step of administering comprises administering an effective amount of a composition comprising an EGFR binding molecule that reduces the activity of the EGFR.

5. The method of claim 4, wherein the EGFR binding molecule comprises an EGFR kinase inhibitor.

6. The method of claim 5, wherein the EGFR kinase inhibitor is selected from the group consisting of gefitinib, erlotinib, 4-(3-chloroanillino)-6,7-dimethoxyquinazoline, EKB-569, EKI-785, canertinib dihydrochloride, D-69491, lapatinib ditosylate, ZD6474, PKC-412, sunitinib malate, vatalanib, SU5614, CEP-701, PKC-412, MLN518, XL999, VX-322, and pharmaceutically acceptable salts thereof.

7. The method of claim 4, wherein the EGFR binding molecule comprises an anti-EGFR antibody.

8. The method of claim 7, wherein the anti-EGFR antibody is selected from the group consisting of cetuximab, ABX-EGF, trastuzumab, and EMD 72000.

9. The method of claim 1, wherein the subject is a mammal.

10. The method of claim 9, wherein the mammal is selected from the group consisting of a rodent, a swine, a ruminant, and a primate.

11. The method of claim 10, wherein the primate is human.

12. A method of treating a disorder associated with obesity in a subject in need of such treatment, the method comprising administering to the subject an effective amount of a compound, wherein the effective amount is effective in reducing an activity of an epidermal growth factor receptor (EGFR) in the subject.

13. The method of claim 12 wherein the disorder associated with obesity is selected from the group consisting of heart disease, hypertension, stroke, Type II diabetes, arthritis, insulin resistance, atherosclerosis, coronary artery disease, hyperlipidemia, gallbladder disease, osteoarthritis, sleep apnea, liver cirrhosis, and cancer.

14. The method of claim 12, wherein the step of administering comprises administering an effective amount of a composition that modulates expression of the EGFR in the subject.

15. The method of claim 14, wherein the composition that modulates expression of the EGFR comprises an antisense oligonucleotide.

16. The method of claim 12, wherein the step of administering comprises administering an effective amount of a composition comprising an EGFR binding molecule that reduces the activity of the EGFR.

17. The method of claim 16, wherein the EGFR binding molecule comprises an EGFR kinase inhibitor.

18. The method of claim 17, wherein the EGFR kinase inhibitor is selected from the group consisting of gefitinib, erlotinib, 4-(3-chloroanillino)-6,7-dimethoxyquinazoline, EKB-569, EKI-785, canertinib dihydrochloride, D-69491, lapatinib ditosylate, ZD6474, PKC-412, sunitinib malate, vatalanib, SU5614, CEP-701, PKC-412, MLN518, XL999, VX-322, and pharmaceutically acceptable salts thereof.

19. The method of claim 16, wherein the EGFR binding molecule comprises an anti-EGFR antibody.

20. The method of claim 19, wherein the anti-EGFR antibody is selected from the group consisting of cetuximab, ABX-EGF, trastuzumab, and EMD 72000.

21. The method of claim 12, wherein the subject is a mammal or a bird.

22. The method of claim 21, wherein the mammal is selected from the group consisting of a rodent, a swine, a ruminant, and a primate.

23. The method of claim 22, wherein the primate is a human.

* * * * *